United States Patent
LeSueur et al.

(10) Patent No.: US 9,181,138 B2
(45) Date of Patent: Nov. 10, 2015

(54) METHODS AND SYSTEMS FOR STABILIZING ORGANIC MATERIAL

(71) Applicant: WISErg Corporation, Redmond, WA (US)

(72) Inventors: Larry LeSueur, Sammamish, WA (US); Jose Lugo, Kirkland, WA (US); Ken Deering, Medina, WA (US); Victor V. Tryon, Woodinville, WA (US); Michael Bridges, Seattle, WA (US); Lee Wilkerson, Stanwood, WA (US); Trevor Lewis, Bellevue, WA (US)

(73) Assignee: WISErg Corporation, Redmond, WA (US)

( * ) Notice: Subject to any disclaimer, the term of this patent is extended or adjusted under 35 U.S.C. 154(b) by 0 days.

(21) Appl. No.: 14/244,729

(22) Filed: Apr. 3, 2014

(65) Prior Publication Data

US 2014/0260464 A1     Sep. 18, 2014

Related U.S. Application Data

(63) Continuation-in-part of application No. 14/205,176, filed on Mar. 11, 2014.

(60) Provisional application No. 61/809,225, filed on Apr. 5, 2013, provisional application No. 61/778,127, filed on Mar. 12, 2013, provisional application No. 61/809,225, filed on Apr. 5, 2013.

(51) Int. Cl.
*C02F 3/02* (2006.01)
*C02F 9/14* (2006.01)
(Continued)

(52) U.S. Cl.
CPC . *C05F 17/00* (2013.01); *C05F 5/00* (2013.01); *C05F 17/0036* (2013.01);
(Continued)

(58) Field of Classification Search
CPC ........... A23V 2300/04; A23V 2300/08; A23V 2300/24; A23V 2300/38; C12P 2203/00; A23K 1/007; C12R 1/865; C12R 1/72; C12R 1/645; C13K 1/01; C13K 1/06; C02F 3/02; C02F 3/34; C02F 3/347; C02D 9/00; B02C 23/18; B02C 23/36; B02D 23/20; C05F 17/00; C05F 17/0036; C05F 17/0063; C05F 17/02; C05F 5/00; C12N 1/16; C12N 1/18; Y02W 30/43
USPC ........ 210/620, 739, 748.16, 766, 87, 89, 104, 210/175, 252, 258, 259; 127/1, 36; 426/7
See application file for complete search history.

(56) References Cited

U.S. PATENT DOCUMENTS
1,597,724 A     8/1926 Cooke
(Continued)

FOREIGN PATENT DOCUMENTS
CA          1061634     * 9/1979
(Continued)

OTHER PUBLICATIONS
Ataei, M. *Irredundant Cover and Semisimplity Condition*. World Academy of Science, Engineering and Technology, 2011, vol. 60, pp. 804-805.
(Continued)

*Primary Examiner* — Nam Nguyen
*Assistant Examiner* — Claire Norris
(74) *Attorney, Agent, or Firm* — Knobbe Martens Olson & Bear LLP

(57) ABSTRACT

The present application relates to systems and methods for processing organic material. The methods may include extraction of biochemical nutrients from organic material, such as food scraps. The method can include comminuting the organic material to form a slurry from components comprising liquid and organic material; combining the slurry with microorganisms, such as a yeast, under aerobic conditions to form a mixture of the slurry and yeast; aerating the mixture; and forming a biomass and a nutrient-rich broth, in which the biochemical nutrients are stabilized and anabolized. The systems may, in some embodiments, be configured to perform the methods of processing organic materials.

20 Claims, 10 Drawing Sheets

(51) Int. Cl.
  *C05F 17/00* (2006.01)
  *C05F 17/02* (2006.01)
  *C12N 1/18* (2006.01)
  *C05F 5/00* (2006.01)
  *C12N 1/16* (2006.01)

(52) U.S. Cl.
  CPC ............ *C05F 17/0063* (2013.01); *C05F 17/02* (2013.01); *C12N 1/16* (2013.01); *C12N 1/18* (2013.01); *Y02W 30/43* (2015.05)

(56) References Cited

U.S. PATENT DOCUMENTS

| | | |
|---|---|---|
| 2,043,265 A | 6/1936 | Roeder |
| 2,146,692 A | 2/1939 | Tiedman |
| 2,178,818 A | 11/1939 | Earp-Thomas et al. |
| 2,209,613 A | 7/1940 | Roeder |
| 2,285,834 A | 6/1942 | Proctor |
| 2,474,833 A | 7/1949 | Eweson |
| 3,014,896 A | 12/1961 | Colwell et al. |
| 3,025,151 A | 3/1962 | Berg |
| 3,462,275 A | 8/1969 | Bellamy |
| 3,711,392 A | 1/1973 | Metzger |
| 3,803,806 A | 4/1974 | Komline, Sr. |
| 3,864,247 A | 2/1975 | Fuchs |
| 3,933,628 A | 1/1976 | Varani |
| 3,981,800 A | 9/1976 | Ort |
| 3,994,780 A | 11/1976 | Klass et al. |
| 4,022,665 A | 5/1977 | Ghosh et al. |
| 4,025,394 A | 5/1977 | Young |
| 4,040,953 A | 8/1977 | Ort |
| 4,137,158 A | 1/1979 | Ishida et al. |
| 4,179,220 A | 12/1979 | Rippon |
| 4,193,786 A | 3/1980 | Brill |
| 4,204,959 A | 5/1980 | Kreuzburg et al. |
| 4,213,857 A | 7/1980 | Ishida et al. |
| 4,233,155 A | 11/1980 | Hawkes et al. |
| 4,248,972 A | 2/1981 | Fischer et al. |
| 4,252,901 A | 2/1981 | Fischer et al. |
| 4,314,904 A | 2/1982 | Fredde et al. |
| 4,316,961 A | 2/1982 | Klass et al. |
| 4,318,993 A | 3/1982 | Ghosh et al. |
| 4,329,428 A | 5/1982 | Ghosh et al. |
| 4,354,936 A | 10/1982 | Ishida et al. |
| 4,400,195 A | 8/1983 | Rijkens |
| 4,424,064 A | 1/1984 | Klass et al. |
| 4,426,450 A * | 1/1984 | Donofrio ...................... 435/243 |
| 4,429,043 A | 1/1984 | Paton |
| 4,442,006 A | 4/1984 | Ishida et al. |
| 4,491,522 A | 1/1985 | Ishida et al. |
| 4,503,154 A | 3/1985 | Paton |
| 4,510,243 A | 4/1985 | Haga et al. |
| 4,529,701 A | 7/1985 | Seely |
| 4,620,928 A | 11/1986 | Gott |
| 4,684,468 A | 8/1987 | DeBaere |
| 4,696,746 A | 9/1987 | Ghosh et al. |
| 4,722,741 A | 2/1988 | Hayes et al. |
| 4,726,899 A | 2/1988 | Stafford et al. |
| 4,735,724 A | 4/1988 | Chynoweth et al. |
| 4,743,287 A | 5/1988 | Robinson |
| 4,765,900 A | 8/1988 | Schwoyer et al. |
| 4,795,711 A | 1/1989 | Nockemann |
| 4,846,975 A | 7/1989 | Kelyman |
| 4,885,094 A | 12/1989 | Srinivasan et al. |
| 4,897,195 A | 1/1990 | Erikson |
| 4,919,813 A | 4/1990 | Weaver |
| 4,975,106 A | 12/1990 | Ferguson |
| 4,981,592 A | 1/1991 | Garbutt et al. |
| 4,985,149 A | 1/1991 | Ohshima et al. |
| 5,015,384 A | 5/1991 | Burke |
| 5,019,265 A | 5/1991 | Herve |
| 5,290,450 A | 3/1994 | Kobayashi |
| 5,354,818 A * | 10/1994 | Vazza ........................ 426/53 |
| 5,377,917 A | 1/1995 | Wiljan et al. |
| 5,409,610 A | 4/1995 | Clark |
| 5,451,319 A | 9/1995 | Kobayashi |
| 5,482,630 A | 1/1996 | Lee et al. |
| 5,500,123 A | 3/1996 | Srivastava |
| 5,525,229 A | 6/1996 | Shih |
| 5,591,342 A | 1/1997 | Delporte et al. |
| 5,630,942 A | 5/1997 | Steiner |
| 5,651,890 A | 7/1997 | Trost |
| 5,656,059 A | 8/1997 | Monster et al. |
| 5,723,048 A | 3/1998 | Kobayashi et al. |
| 5,798,043 A | 8/1998 | Khudenko |
| 6,019,900 A | 2/2000 | Brink et al. |
| 6,291,232 B1 | 9/2001 | Miller, III |
| 6,409,788 B1 | 6/2002 | Sower |
| 6,444,126 B1 | 9/2002 | Gates et al. |
| 6,447,681 B1 | 9/2002 | Carlberg et al. |
| 6,632,362 B2 | 10/2003 | Miller, III |
| 6,682,578 B2 | 1/2004 | Sower |
| 6,790,359 B2 | 9/2004 | Miller, III |
| 6,811,701 B2 | 11/2004 | Wilkie |
| 6,846,343 B2 | 1/2005 | Sower |
| 6,866,779 B1 | 3/2005 | Burke |
| 6,893,572 B2 | 5/2005 | Burke |
| 6,942,798 B2 | 9/2005 | Miller, III |
| 7,153,428 B2 | 12/2006 | Chynoweth et al. |
| 7,297,274 B2 | 11/2007 | Wilkie |
| 7,402,247 B2 | 7/2008 | Sutton |
| 7,410,583 B2 | 8/2008 | Gray et al. |
| 7,416,669 B1 | 8/2008 | Carolan et al. |
| 7,442,224 B2 | 10/2008 | Porubcan |
| 7,452,466 B2 | 11/2008 | Binning et al. |
| 7,540,961 B2 | 6/2009 | Hansen et al. |
| 7,641,796 B2 | 1/2010 | Stroot et al. |
| 7,708,885 B2 | 5/2010 | Lanting et al. |
| 7,806,957 B1 | 10/2010 | Burke |
| 8,221,626 B2 | 7/2012 | Sassow |
| 2003/0141244 A1 | 7/2003 | Hansen et al. |
| 2004/0025715 A1 | 2/2004 | Bonde et al. |
| 2005/0113611 A1 | 5/2005 | Adams et al. |
| 2005/0252855 A1 | 11/2005 | Shieh et al. |
| 2006/0081534 A1 * | 4/2006 | Dimitriou et al. ............ 210/620 |
| 2007/0289922 A1 | 12/2007 | Ladron de Guevara et al. |
| 2009/0017164 A1 * | 1/2009 | Schisler et al. ................. 426/62 |
| 2009/0282882 A1 | 11/2009 | Verhave et al. |
| 2009/0299513 A1 | 12/2009 | Suh et al. |
| 2011/0153395 A1 | 6/2011 | Ohno |
| 2011/0165035 A1 | 7/2011 | Lewis et al. |
| 2011/0238600 A1 | 9/2011 | Lee |
| 2012/0265336 A1 | 10/2012 | Mallett et al. |
| 2012/0315668 A1 * | 12/2012 | Lopez-Cervantes et al. ... 435/42 |
| 2013/0266556 A9 | 10/2013 | Marshall Medoff |
| 2013/0323824 A1 | 12/2013 | Chun |

FOREIGN PATENT DOCUMENTS

| | | |
|---|---|---|
| JP | 6-233991 A | 8/1994 |
| JP | 2002-272491 | 9/2002 |
| KR | 20100040076 | 4/2010 |
| KR | 10-2011-0140111 | 12/2011 |
| WO | WO 2009/119961 A1 | 10/2009 |
| WO | WO 2012/069839 | 5/2012 |

OTHER PUBLICATIONS

Sreethawong, T. et al., *Hydrogen Production from Glucose-Containing Wastewater Using an Anaerobic Sequencing Batch Reactor: Effects of COD Loading Rate, Nitrogen Content, and Organic Acid Composition.* Chemical Engineering Journal, May 2010, vol. 160, pp. 322-332.

International Search Report and Written Opinion for International Application No. PCT/US2011/045401 mailed Oct. 25, 2011.

International Search Report for International Patent No. PCT/US2014/023269 dated Jun. 24, 2014.

* cited by examiner

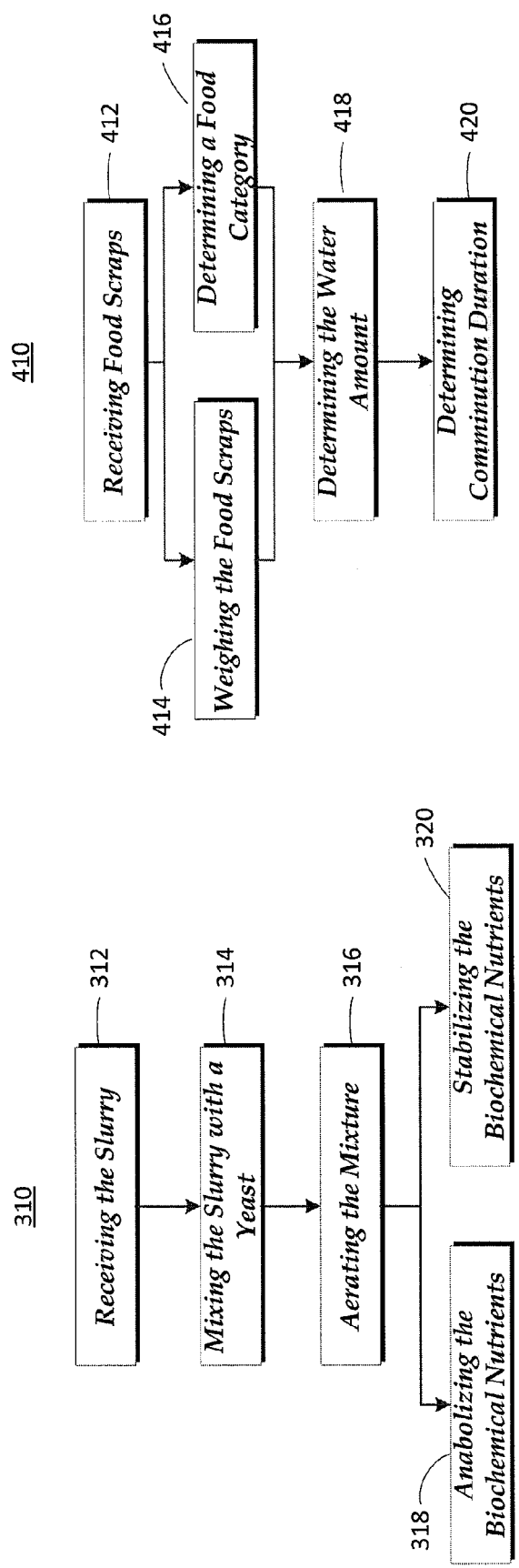

METHODS AND SYSTEMS FOR STABILIZING ORGANIC MATERIAL

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 C.F.R. §1.57.

BACKGROUND

Description

Food scraps are an accepted consequence of the food production cycle in our society. Food scraps can be a product of any step in the food supply chain. Food scraps can originate from farms, grocery stores, food transportation companies, food processing companies, restaurants and other like businesses, and even from our homes. Food scraps are the remnant organic materials from the food supply chain that are not ultimately consumed. Food scraps may be variously referred to as putrescible waste, pre- or post-consumer food waste, or a component of organic waste. Food scraps are the primary embodiment of these systems and methods, but are intended to be applied to organic material with high nutritive value and prior to the onset of uncontrolled rot or decay associated with the term putrescible waste.

The process of putrification is the result of metabolic activity of microorganisms naturally found on the surface of the vegetable food scraps or microbial cross-contaminants from animal processing that colonize or reside on the surface of animal products. Putrification is the process that results in rapid, uncontrolled decay of food scraps and results in foul smelling organic compounds that may also act as attracts for disease-spreading vermin including insects and mammals. Putrification is often qualitatively characterized by evolution of volatile fatty acids and foul smelling polyamines and hydrogen sulfide. Such compounds and gases can easily be identified and quantified in the laboratory using specialized instrumentation. Prevention of the rapid loss of the valuable, high-energy nutritive biochemicals is the intent of the systems and methods claimed herein. Since the inherent thermodynamic energy and nutritive value is lost in putrid waste, it is unsuitable for the disclosed processes and methods found herein.

Considering a grocery store as the origin of organic waste, for example, in the normal course of business a grocery store may throw away a significant amount of food scraps that are not suitable for human consumption, past their expiration date, or is not aesthetically pleasing for display in the grocery store. The food scraps are consequently collected from the various departments of the grocery store and disposed of in a dumpster behind the grocery store. Similar collection and disposal occurs in other locations along the food supply chain, with similar results—the food scraps being thrown away with loss of nutritive value.

The food scraps, once disposed of, naturally begin to decompose as the microorganisms (e.g., bacteria, fungi) on the food scraps proliferate and metabolize, causing the food scraps to rot and stink. Vermin, such as rats and other rodents, as well as flies, are attracted to such rotting food scraps. The smell of the rotting food scraps and the presence of the vermin and flies can be a significant nuisance and potential public health hazard to a grocery store and its employees and neighbors, as well as any other location in the food supply chain.

Thus, to deal with the nuisance of rotting and stinking food scraps, a grocery store must have the food scraps hauled away at regular intervals. Such removal costs are increasingly expensive and are borne by the grocery store as a recurring cost.

Food scraps will rot and decompose after disposal because the existing microorganisms on the food scraps grow rapidly and decompose the cellular structure (e.g., cellulose, etc.) and the biochemical nutrients (e.g., vitamins, carbohydrates, lipids, proteins, etc.) that make up the food. Decomposition by the microorganisms involves the breakdown of organic material into simpler carbon molecules, ultimately producing acids, methane, hydrogen sulfide, and carbon dioxide. This decomposition of the organic material in the food scraps to simpler molecules is referred to as catabolism.

Food scraps are disposed of in a number of ways. Often the food scraps are disposed of in a regular landfill along with non-organic garbage or mixed with yard waste or land-clearing waste for conversion to compost. In the United States alone some 34 million tons of food scraps is produced each year and nearly 33 million tons is committed to landfills for disposal. However, decomposing food waste is a nuisance and presents environmental issues, such as pollution hazards and nuisance issues. Rainwater percolates through landfills, where food waste is deposited, and leads to heavy metals and minerals leaching, thus contributing to the contamination of soils, surface water and ground water. Decaying waste emits greenhouse gases which subsequently cause significant environmental concern.

Beyond landfill disposal, attempts have been made to address the environmental concerns and capitalize on the catabolic degradation of food scraps. One approach has been to conduct processing of the food scraps using selected bacteria in an anaerobic environment to enhance the catabolic process. This process of anaerobic digestion attempts to capture the methane produced from the catabolic process and use the captured methane as an energy source. However, methane capture from food scraps recycling has proven to be extremely inefficient and has, in some instances, been a net negative source of energy. Methane capture via anaerobic processing also still requires the grocery store or other location in the food supply chain to pay high disposal fees for removal and transport of the food scraps to the anaerobic digestion facility.

Another approach to dealing with the food scraps has been to compost the food scraps. Composting is a human-controlled biological decay process that turns the food scraps into heat, carbon dioxide, ammonium, and incompletely decayed organic matter. The result of the controlled decay process is a humus-like material that is most often used as a soil amendment. The compost is characterized more by its value as a soil amendment resulting in greater moisture carrying capacity, than its intrinsic nutritive value. In addition the nitrogen containing compounds produced by composting can be used to produce fertilizer. However, significant amounts of the nutrients in the original food scraps are lost in the catabolic process resulting in the wasteful production of heat and carbon dioxide. Composting, like methane capture through anaerobic digestion, also still requires the grocery store or other location in the food supply chain to pay high disposal fees for removal and transport of the food scraps.

Many other systems and methods have been described for disposal of food scraps/organic waste. These systems generally consist of methods for decreasing bulk volume of the waste and a) use of the shredded food waste as animal feed or b) disposal through the sanitary sewer system where the organic material is again catabolized (controlled or uncontrolled) by microorganisms from many different Domains and Phyla. Disposal in this manner results in much of the carbon and nitrogen material being lost through carbon dioxide or methane. Disposal of organic through the sanitary sewer system transfers the hazards and problems of decaying food waste to the local or regional water treatment plant, but ultimately results in the loss of thermodynamic energy in the food scraps and the generation of greenhouse gases.

Thus, previous attempts at addressing the nuisance of food scraps have sought value in the transport and disposal in landfills (so-called tipping fees) or in catabolic (degradative) byproducts of the decomposed food scraps such as methane capture.

BRIEF DESCRIPTION OF THE DRAWINGS

FIG. 3 is a flow diagram illustrating one example for anabolizing and stabilizing biochemical nutrients within the scope of the present application.

FIG. 4 is a flow diagram illustrating one example for determining the water amount and comminution duration for extracting the biochemical nutrient content of food scraps into a slurry.

DETAILED DESCRIPTION

The systems and methods disclosed may be applied to organic material generally, particularly to organic material having high nutritive value and prior to the onset of uncontrolled rot or decay associated with putrescible waste. The systems and methods may be described herein with regard to food scraps as an embodiment of the organic material contemplated. Despite being considered unsuitable for human or animal consumption, food scraps contain a high level of valuable nutrition which can be extracted, stabilized, and reused in controlled anabolic processes. The food scraps can yield nutrient-rich materials that may have various agricultural uses. Rather than allow the biochemical nutrients found in food scraps to catabolize and utilize only the catabolic products of the food scraps, the systems and methods disclosed herein capture both the inherent thermodynamic energy of complex biomolecules, as well as, the nutritive value of the biochemical compounds found in the food scraps before the nutrients can be lost to natural catabolic processes.

The disclosure provides systems and methods that capitalize on the available biochemical nutrients found in food scraps by extracting the biochemical nutrients from food scraps before the nutrients are degraded or catabolized by harmful microorganisms. Following extraction, the biochemical nutrients found in food scraps can be stabilized or then processed anabolically and utilized by specially selected, and seeded beneficial microorganisms. This uniform, increased biomass can be harvested and held for later processing into valuable products, such as plant fertilizer, soil amendment, organic fertilizer, and other downstream agricultural or consumer products.

Systems and methods disclosed herein involve the extraction of biochemical nutrients from organic waste, such as food scraps. The food scraps can be comminuted in the presence of water to extract the biochemical nutrients and produce a slurry of organic particulate matter. The amount of water provided to the comminution device may be a function of a food category of the food scraps and may be a function of the weight or amount of food scraps being comminuted.

Systems and methods disclosed herein involve the aerobic respiration of a beneficial microorganism, such as single-cell yeast, to stabilize or anabolize the biochemical nutrients extracted from the organic waste. Once the biochemical nutrients have been extracted from the organic waste the nutrients can be mixed with the beneficial microorganism(s) under aerobic conditions to stabilize the nutrients in solution and also used to produce a nutrient-rich biomass of selected and cultured microorganisms.

Figure 1:
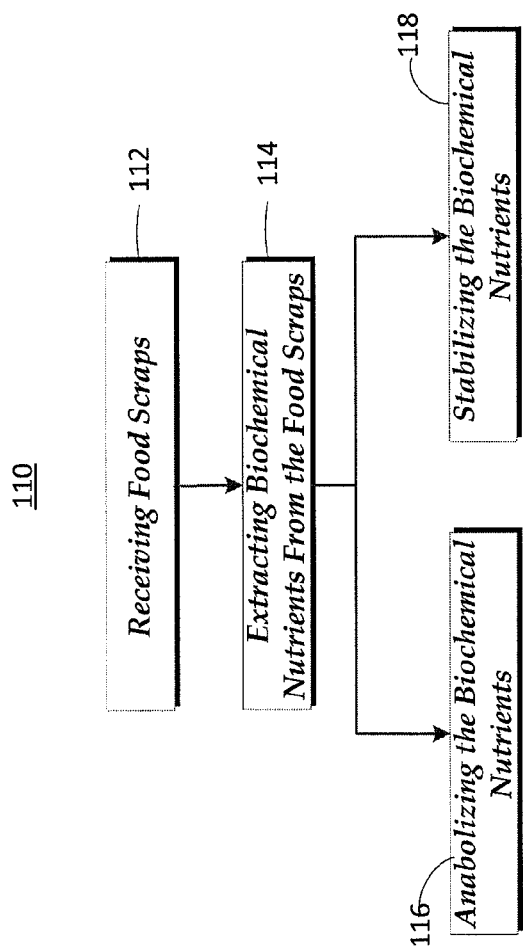
FIG. 1 is a flow diagram illustrating one example of salvaging the biochemical nutrients in food scraps within the scope of the present application.

FIG. 1 is a flow diagram representing one example of the method 110 for using organic waste, such as, for example food scraps, received from a source in the food supply chain, to salvage the biochemical nutrients in the organic waste. As illustrated in FIG. 1, method 110 may include one or more functions, operations, or actions as illustrated by one or more operations 112-118. Operations 112-118 may include the "Receiving Food Scraps" operation 112, "Extracting the Biochemical Nutrients from the Food Scraps" operation 114, "Anabolizing the Biochemical Nutrients" operation 116, and "Stabilizing the Biochemical Nutrients" operation 118.

Method 110 may begin at operation 112, "Receiving Food Scraps." In operation 112, food scraps are received for processing. The food scraps received in operation 112 may originate from any location along the food supply chain. For example, the food scraps received may come from an agricultural farm, dairy farm, food processing business, food transportation business, grocery store, warehouse store, restaurant, residence, and the like.

Non-limiting examples of food scraps that may be received in operation 112 include, for example, pre- or post-consumer food scraps. Some examples of food scraps include, but are not limited to, dairy (e.g., milk, cheese, etc.), meat (e.g., poultry, beef, fish, pork, etc.), grains (e.g., bread, crackers, pasta), fruits, and vegetables. Illustratively, food scraps can correspond to a variety of food types or categorizations of food. As one example, the food scraps may be unsold or expired food from a food retailer. As another example, food scraps may be uneaten food or scraps from a restaurant or the delicatessen section of a grocery store. As another example, the food scraps may be uneaten or leftover food from a residence, such as a home, dormitory, or apartment complex. In one embodiment, the food scraps can include other organic material, such as, for example, flowers or house plants, etc.

Operation 112 may be followed by operation 114, "Extracting Biochemical Nutrients from Food Scraps." The food scraps received in operation 112 may contain biochemical nutrients in their highest thermodynamic state before the nutrients have become subject to metabolic degradation (e.g., catabolism) brought about by microorganisms such as bacteria and fungi. The methods and systems are appropriate for extracting the biochemical nutrients from the food scraps before the nutrients are catabolized. Extracting the biochemical nutrients in the highest thermodynamic state retains both the energy value and the nutritive value of the biochemical compounds and allows the nutrients to be used or recovered downstream in a variety of applications. Additionally, by extracting the biochemical nutrients before degradation of the nutrients begins in any significant manner, the food scraps may be prevented from rotting and stinking. Maintaining a clean, vermin- and odor-free environment can be a significant benefit to the producer of the food scraps. Systems and methods for extracting the biochemical nutrients from the food scraps are described in further detail herein.

Biochemical nutrients that can be extracted from the food scraps include, but are not limited to, the following: proteins and amino acids, lipids and fatty acids, carbohydrates and simple sugars, vitamins and hormones, fiber, cellulose, nucleic acids and polyamines, etc. In a review of the class and functions of biochemical products in plants, it is suggested that the number of known plant chemicals range from 2,750 to 5,000. (Chemical from Plants; N J Walton and D E Brown, EDS; 1999; World Scientific Press; Chapter 1; Classes and Functions of Secondary Products from Plants; Jeffrey B. Harbone; pp. 1-26)

Operation 114 may be followed by operation 116, "Anabolizing the Biochemical Nutrients" and/or operation 118, "Stabilizing the Biochemical Nutrients." Once the biochemical nutrients are extracted from the food scraps, the nutrients can be anabolized or stabilized in some fashion to maintain or enhance the thermodynamic state of the biochemical nutrients and prevent the nutrients from degrading. Stabilization and anabolization of the biochemical nutrients allows the nutrients to be later processed and used in this stable or enhanced thermodynamic state.

Regarding operation 116, anabolization of the biochemical nutrients can involve using beneficial microorganisms in a specific environment and under certain conditions to take up the biochemical nutrients to form new biochemical nutrients and to promote cell division and growth of the microorganisms. Anabolization, as disclosed herein, involves forming a biomass of living material made up of the microorganisms in which the microorganisms can be sustained and made available for later utilization in further processing. Thus, the microorganisms may use the biochemical nutrients extracted from the food scraps as nutrition to intracellularly build new biochemical and cellular infrastructure, allowing the microorganisms to multiply through cellular division. Anabolization of the biochemical nutrients into a biomass may be facilitated under aerobic conditions through aerobic respiration of the microorganisms.

In one non-limiting example, a yeast or other fungi can be used as the beneficial microorganism to anabolize the biochemical nutrients. As the aerobic respiration of the yeast is facilitated by the extracted nutrients from the food scraps, both the mass and quantity of the yeast in the biomass can increase. In one example, the number of yeast may increase 100 fold over a 7-10 day time period, with a two-fold increase in biomass (dry weight) of individual organisms.

One example of a yeast that may be use to anabolize the extracted biochemical nutrients into a biomass is *Saccharomyces cerevisiae*. Under anaerobic conditions, *S. cerevisiae*, will ferment simple sugars, converting the sugars to acids, gases, and/or alcohols as toxic end products of metabolism. However, under aerobic conditions, a *S. cerevisiae* are able to anabolize the sugars, taking the sugars up and using the sugars and oxygen for sustainable respiration and growth. Unlike the regular disposal of food scraps as garbage, which facilitates degradation of the biochemical nutrients within hours of disposal, the extracted biochemical anabolized into a biomass can be maintained for several weeks, using the herein described systems and methods. Other yeasts may be used under aerobic conditions to facilitate anabolization and stabilization of the biochemical nutrients, such as microorganisms in the Domain Fungi and Phylum Ascomycota, including *Candida* (Yarrowia) *lipolytica* and *Candida utilis*.

Regarding operation 118, "Stabilizing the Biochemical Nutrients," stabilization of the biochemical nutrients can involve using certain beneficial microorganisms under certain conditions to maintain and stabilize the biochemical nutrients in a nutrient-rich broth which prevents the biochemical nutrients from catabolizing. It was discovered that the *S. cerevisiae* is able to stabilize the biochemical nutrients that are not anabolized by the microorganisms, thus forming a nutrient-broth of biochemical nutrients. Without being confined to any particular theory as to the mechanism, it was discovered that in the presence of *S. cerevisiae* under aerobic conditions, the extracted biochemical nutrients do not putrefy, rot, or stink. Unlike the disposal of food scraps as garbage, which facilitates degradation of the biochemical nutrients within hours of disposal, the extracted biochemical held in a nutrient-rich broth can be stabilized for several weeks.

Figure 2:
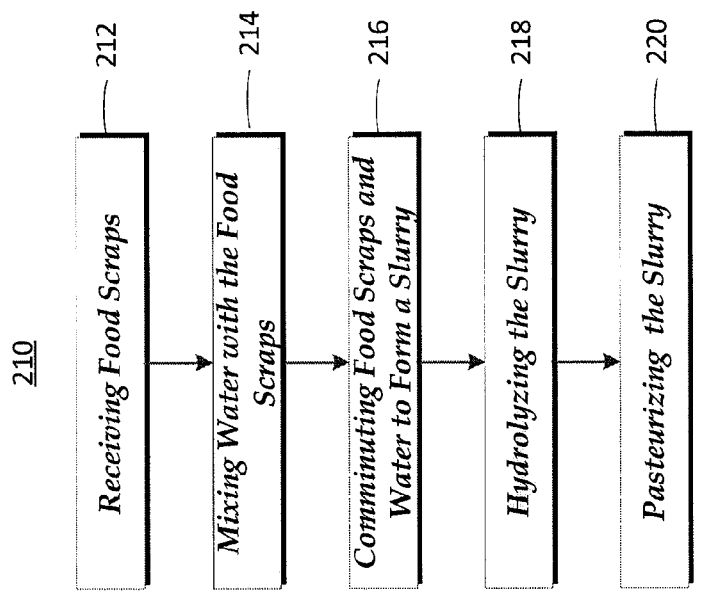
FIG. 2 is a flow diagram illustrating one example for extracting the biochemical nutrient content of food scraps within the scope of the present application.

FIG. 2 is a flow diagram representing one example of a method 210 for extracting the biochemical nutrient content of food scraps within the scope of the present application. As illustrated in FIG. 2, method 210 may include one or more functions, operations, or actions as illustrated by one or more operations 212-220. Operations 212-220 may include the "Receiving Food Scraps" operation 212, "Mixing Water With the Food Scraps" operation 214, "Comminuting the Food Scraps and Water to Form a Slurry" operation 216, "Hydrolyzing the Slurry" operation 218, and "Pasteurizing the Slurry" operation 220. The method 210 shown in FIG. 2 can be an embodiment of the operation 114 ("Extracting Biochemical Nutrients from the Food Scraps") shown in FIG. 1. Like operation 114, method 210 is a particular method for extracting biochemical nutrients from food scraps.

In FIG. 2, operations 212-220 are illustrated as being performed sequentially, with operation 212 performed first and operation 220 performed last. It will be appreciated however that some operations may be re-ordered as convenient to suit particular embodiments, and that some operations may be performed concurrently in some embodiments. It will also be appreciated that some operations are optional to the successful completion of method 210.

Method 210 may begin at operation 212, "Receiving Food Scraps." Operation 212 can correspond to operation 112 of method 110 in FIG. 1. In operation 212, food scraps are received for processing. The food scraps received in operation 212 may originate from any location along the food supply chain.

Operation 212 may be followed by operation 214, "Mixing Water with Food Scraps." The water may be added to the food scraps received before, during, and/or after the food scraps are comminuted, as discussed below. The water may be, for example, potable water from a municipal water source or a well. The water may be, for example, stored in a tank. The temperature of the water supplied to the food scraps can be sufficiently high to assist in the hydrolysis of the food scraps and emulsification of any lipids in the food scraps. In one embodiment, the temperature of the water mixed with the food scraps can be, for example between ambient temperature and 200° F. For example, in one embodiment, the temperature of water mixed with the food scraps can be 140° F., which is the minimum food safe temperature. Using water with an elevated temperature can be beneficial in killing harmful microbes and bacteria residing on the food scraps.

The relative amount of water mixed with the food scraps may vary depending upon multiple factors, such as the amount (e.g., weight) of the food scraps received. The relative amount of water mixed with the food scraps may also vary depending on the type of food, or food category, received for processing. As discussed in detail below with relation to FIG. 3, the amount of water mixed with the food scraps can be optimized to prepare the resultant slurry for aerobic anabolization and stabilization conditions.

Operation 214 may be followed by operation 216, "Comminuting the Food Scraps and Water to Form a Slurry." In operation 214, the food scraps can be formed into a slurry through comminuting the food scraps. In one embodiment, the water is mixed with the food scraps during comminution of the food scraps. In another embodiment, the water is mixed with the food scraps prior to comminution of the food scraps. In some embodiments, the food scraps may be reduced to liquid and small particulates (e.g., through comminution). The particulates of the slurry can be the solid food particles remaining after the slurry is formed and the particulates may become suspended in the liquid composition. As comminution continues, and the food scraps are broken down, a slurry can begin to form. The slurry formation may be assisted by the presence of the water added to the food scraps. Thus, the slurry can be a mixture of the resultant particulates of food scraps following comminution and the water added to the food scraps, such that the biochemical nutrients and other material released from the food scraps are a part of the liquid composition.

Any suitable method for comminuting the organic materials can be used. For example, the food scraps may be subjected to grinding, cutting, crushing, milling, macerating, hydro-pulping, and the like. In the process of comminution, the pieces of individual food scraps can be broken into smaller and smaller particulates by the shear force of the comminution process until the desired particulate size is reached. Comminution can break down the structure of the food scraps. The shear forces applied to the particulates of the food scraps can break apart the extracellular material holding the food scraps together. In the process of breaking the food scraps into smaller and smaller pieces, the organic cellular material of the cells can be become exposed to the shear forces of a specially selected comminution device. The shear forces can lyse the cells to release the biochemical nutrients into the water added to the food scraps and the resultant slurry being formed. The process of comminution results in a very rapid release of the biochemical nutrients found in the food scraps. As discussed below, the biochemical nutrients can be released into the slurry in a matter of minutes. This near-instantaneous release of the nutrients is contrasted with composting, which requires several weeks to accomplish the extraction of nutrients from the decomposing food scraps.

The size of the particulate formed from the food scraps in comminution may vary and may be selected, in part, based upon the downstream requirements for stabilizing and anabolizing the extracted biochemical nutrients. In one embodiment, the target particulate size resulting from comminution can be based on the intent to extract as much of the biochemical nutrients from the food scraps as possible. The particulate resulting from comminution may have an average size of, for example, no more than about 10 mm; no more than about 8 mm; no more than about 5 mm; no more than about 3 cm; or no more than about 1 mm. The particulates may have an average size of, for example, at least about 500 µm; at least about 1 mm; at least about 2 mm; at least about 3 mm; at least about 5 mm; at least about 8 mm; and at least about 10 mm. In some embodiments, the particulates have an average size of about 1 mm to about 5 mm. Non-limiting examples for the average particle size include about 2 mm, about 3 mm, about 5 mm, about 8 mm, or about 10 mm. As discussed in detail below with relation to FIG. 3, the duration of comminution can be optimized to prepare the resultant slurry for aerobic anabolization and stabilization conditions. If the particulate size is too large, aeration of the mixture of the slurry and the yeast may be difficult, as discussed below.

The amount, or total solids, of solid organic material (e.g., the particulates) remaining in the slurry following comminution of the food scraps may be, for example, at least about 1% (w/w); at least about 5% (w/w); at least about 10% (w/w); at least about 15% (w/w); at least about 20% (w/w); or at least about 25% (w/w). The amount of organic material in the slurry may be, for example, no more than about 25% (w/w); no more than about 20% (w/w); no more than about 15% (w/w); no more than about 10% (w/w); no more than about 5%; no more than about 1%. In some embodiments, the amount of organic material in the slurry is from about 5% to about 15%. Non-limiting examples for the amount of solid organic material in the slurry include about 5% (w/w), about 6% (w/w), about 7% (w/w), about 8% (w/w), about 9% (w/w), about 10% (w/w), about 11% (w/w), about 12% (w/w), about 13% (w/w), about 14% (w/w), or about 15% (w/w).

Operation 216 can be followed by operation 218, "Hydrolyzing the Slurry." Operation 218 allows for the hydrolysis of the particulates in the slurry and can further enhance extraction of the biochemical nutrients from the food scraps into the slurry. During operation 218, the slurry can be treated with hydrolytic enzymes to hydrolyze the particulate organic material in the slurry. The hydrolytic enzymes can act to further break down the particulate matter by degradation of the organic structural material binding the particulates and can thus release additional biochemical nutrients into the slurry. Hydrolytic enzymes that can used during operation 218 include, but are not limited to, proteases, lipases, disaccharidases, cellulases, lignocellulases, and the like.

Operation 218 can be followed by operation 220, "Pasteurizing the Slurry." Operation 220 allows for pasteurization of the biochemical nutrients and particulates in the slurry in order to sterilize the slurry and reduce the number of viable pathogens (e.g., microbes) in the slurry. Pasteurizing the slurry can be accomplished by heating the slurry to a specific temperature for a predefined length of time and, if necessary to protect a particular component, immediately cooling it. It will be appreciated that a side effect of pasteurizing the slurry is that some vitamin and mineral content may be lost to degradation. However, because the loss of nutrients is small in comparison to the large amount of biochemical nutrients remaining in the slurry, pasteurization provides a viable approach to reducing the numbers of pathogenic microorganisms in the slurry prior to anabolizing and stabilizing the biochemical nutrients.

Any method suitable for pasteurizing the slurry can be used. The skilled artisan, guided by the teachings of the present application, can identify appropriate temperatures and time periods for heating in order to pasteurize the slurry. In some embodiments, the pasteurizing can include heating the slurry at a pre-determined temperature for a pre-determined period of time. In some embodiments, the pre-determined temperature and pre-determined period of time are effective to reduce microbial activity in the slurry. In some embodiments, the slurry is maintained at a temperature in a range of about 140° F. to about 200° F. during pasteurization. For example, the temperature of the slurry may be maintained at a temperature of at least about 140° F.; at least about 150° F.; at least about 160° F.; at least about 170° F.; at least about 180° F.; at least about 190° F.; at least about 200° F. In some embodiments, the temperature of the slurry may be maintained at a temperature of no more than about 140° F.; no more than about 150° F.; no more than about 160° F.; no more than about 170° F.; no more than about 180° F.; no more than about 190° F.; no more than about 200° F.

The period of time for heating the slurry during pasteurization can be between about 5 minutes to about 30 minutes. For example, the slurry may be heated for at least about 5 minutes; for at least about 10 minutes; for at least about 15 minutes; or for at least about 20 minutes. Likewise, in some embodiments, the slurry may be heated for no more than about 5 minutes; for no more than about 10 minutes; for no more than about 15 minutes; or for no more than about 20 minutes. The skilled artisan will readily understand the variable combinations of temperature and time period can be used to effectively pasteurize the slurry. In one non-limiting example, the temperature of the slurry can be maintained at a temperature of 180° F. for a period of between about 10 minutes to 20 minutes for successful pasteurization of the slurry.

Although operation 218, hydrolyzing the slurry, is shown in FIG. 2 as being performed prior to operation 220, pasteurizing the slurry, the operation of pasteurizing the slurry may also be performed before the operation of hydrolyzing the slurry. Also, in certain embodiments, pasteurizing the slurry can be performed concurrently with hydrolyzing the slurry. In this manner, the hydrolysis of the slurry and the pasteurization of the slurry can be conducted in the same physical location under the same physical conditions, and also at the same time. In some embodiments, the slurry may be pasteurized without also hydrolyzing the slurry. In some embodiments, the slurry may hydrolyzed without also pasteurizing the slurry. It will be appreciated that operations 218 and 220 follow the operation of comminuting the food scraps in operation 216 in which the biochemical nutrients are extracted from the food scraps. Thus, in this regard, operations 218 and 220 are optional to the completion of method 210 shown in FIG. 2, and may be excluded from the method. In one embodiment, operations 218 and 220 are not performed and instead the slurry resulting from comminuting the food scraps in operation 216 is immediately available for further processing or for anabolization and stabilization.

FIG. 3 is a flow diagram representing one example of a method 310 for anabolizing and stabilizing biochemical nutrients within the scope of the present application. As illustrated in FIG. 2, method 310 may include one or more functions, operations, or actions as illustrated by one or more operations 312-320. Operations 312-320 may include the "Receiving Food Scraps" operation 312, "Mixing the Slurry with a Yeast" operation 314, "Aerating the Mixture" operation 316, "Anabolizing the Biochemical Nutrients" operation 318, and "Stabilizing the Biochemical Nutrients" operation 320. The method 310 shown in FIG. 3 may be a particular embodiment of the operations 116 and 118 shown in FIG. 1.

In FIG. 3, operations 312-320 are illustrated as being performed sequentially, with operation 312 performed first and operation 320 performed last. It will be appreciated however that some operations may be re-ordered as convenient to suit particular embodiments, and that some operations may be performed concurrently in some embodiments. It will also be appreciated that some operations are optional to the successful completion of method 310.

Method 310 may begin at operation 312, "Receiving the Slurry." In operation 312, a slurry of biochemical nutrients and food particles is received for anabolization and stabilization of the biochemical nutrients found in the slurry. The slurry received in operation 312 may be a slurry of particulates suspended or mixed in a liquid solution and the liquid solution may also contain biochemical nutrients. The slurry may be received from operations performed in method 210 in which the biochemical nutrients are extracted from food scraps. Thus, the slurry received in operation 312 may be a derivative or result of operation 216, 218, or 220 in method 210, shown in FIG. 2. Alternatively, the slurry may instead be received from other operations or methods. The slurry received in operation 312 may be a collection or combination of different slurries produced from different batches of food scraps and now combined in method 310.

Operation 314 may be followed by operation 314, "Mixing the Slurry with a Yeast." In operation 314, the slurry received is mixed with a yeast. In one embodiment, the slurry is mixed with the yeast is *Saccharomyces cerevisiae*. *S. cerevisiae* is a eukaryotic single-cell species of yeast and a member of the fungi kingdom. In one embodiment, the slurry received in operation 312 may be added to an existing batch of yeast already in solution and that had been previously used to anabolize and stabilize a previous batch of slurry. In another embodiment, fresh or a new species of yeast may be added to the slurry. The slurry and the yeast may be mixed together in any manner sufficient to achieve homogeneity between the slurry and the yeast. In one embodiment, the yeast and the slurry may be stirred in order to achieve homogeneity of the mixture. In another embodiment, the yeast and the slurry may be mixed through air lift or bubbling of the mixture, such as through aeration of the mixture, as discussed below. The amount of yeast mixed with the slurry may depend on the quantity of food scraps initially received. In one embodiment, the amount of yeast mixed can be approximately 100,000 organisms per ml (final volume) or 1,000,000 organisms per ml or 10,000,000 organisms per ml.

Operation 314 may be followed by operation 316, "Aerating the Mixture." Aerating the mixture may involve supplying oxygen to the mixture of the yeast and slurry. Under anaerobic or otherwise unfavorable conditions, *S. cerevisiae*, can ferment or otherwise degrade the biochemical nutrients in the slurry. However, it was discovered that under aerobic conditions, such degradation of the biochemical nutrients in the slurry does not occur. Aeration of the mixture of yeast and slurry can be accomplished in any manner to sufficiently distribute the oxygen through the mixture. In one embodiment, aeration of the mixture can be accomplished by diffused aeration, by pumping compressed air under the mixture and allowing the air to bubble up or diffuse back up through the mixture. In one embodiment, aeration of the mixture by diffused aeration also acts to homogenously mix the mixture. Thus, in one embodiment, operations 314 and 316 can be accomplished through a single step of aerating the mixture, such that the aeration process provides the requisite oxygen to the mixture and also acts to mix the yeast with the biochemical nutrients.

The oxygen content of the mixture can be varied to optimize the stabilization and anabolization conditions for the biochemical nutrients. For example, the extent to which the mixture is aerated can be adjusted to maintain a desired oxygen content in the mixture. Furthermore, the extent of aeration can be adjusted to maintain the mixture in a quiescent condition. For example, if the mixture is vigorously aerated, too much oxygen may be provided to the mixture and may unintentionally stimulate the metabolic activity of the remaining detrimental microbes (e.g., bacteria) in the mixture, causing the microbes to out-grow (out-compete) the yeast. Aeration can be performed at ambient temperature and pressure. The process may be described as an open vessel, aerobic, closed loop system.

To optimize the stabilization and anabolization conditions for the biochemical nutrients, the dissolved oxygen content in the mixture may be maintained at, for example, at least about 0.5 ppm (parts-per-million); at least about 1 ppm; at least about 2 ppm; at least about 3 ppm; at least about 4 ppm; at least about 5 ppm; at least about 6 ppm; at least about 7 ppm; or at least about 8 ppm. The dissolved oxygen content in the mixture may be maintained at for example, no more than about 8 ppm; no more than about 7 ppm; no more than about 6 ppm; no more than about 5 ppm; no more than about 4 ppm; no more than about 3 ppm; no more than about 2 ppm; no more than about 1 ppm; or no more than about 0.5 ppm. In some embodiments, the oxygen content in the mixture is maintained at between about 1 ppm and 3 ppm. Non-limiting examples for the oxygen content in the mixture include about 0.5 ppm, about 1 ppm, about 1.5 ppm, about 2 ppm, about 2.5 ppm, or about 3 ppm.

As discussed above, the particulate size of the organic material in the slurry can be maintained below a desired diameter. If the particulate size is too large, aeration of the mixture of the slurry and the yeast may be difficult because the aeration process may be unable to lift any larger organic particles. Thus, it may be of significant importance to obtain a desired particulate size following comminution of the food particles in order to sufficiently extract the biochemical nutrients form the food scraps, but also to ensure that the mixture of the slurry and the yeast can be sufficiently aerated.

Operation 316 may be followed by operations 318 and 320, "Anabolizing the Biochemical Nutrients," and "Stabilizing the Biochemical Nutrients," respectively. Anabolization and stabilization of the biochemical nutrients can be a result of the optimized aeration and mixing of the yeast in the presence of the biochemical nutrients in the slurry. Through anabolization and stabilization of the biochemical nutrients extracted from the food scraps, the nutrients that might otherwise be lost to catabolism can be preserved and utilized in a variety of valuable ways. For example, the nutrients can be processed downstream and used to make and enhance agricultural fertilizer. Operation 318 can correspond to operation 116 of method 110 in FIG. 1 and operation 320 can correspond to operation 118 of method 110 in FIG. 1.

As discussed above with relation to operation 116 in FIG. 1, anabolization of the biochemical nutrients, such as in operation 318, can involve using the yeast to take up the biochemical nutrients to form new biochemical nutrients and to promote cell division and growth of the yeast. Anabolization, can involve the formation of a biomass of yeast in which the yeast are sustained and made available for later utilization in further processing, to form, for example, fertilizers and other agriculturally-useful products.

As discussed above with relation to operation 118, stabilization of the biochemical nutrients, such as in operation 320, can involve using the yeast under aerobic conditions to maintain and stabilize the biochemical nutrients in a nutrient-rich broth. Maintaining the biochemical nutrients in this elevated thermodynamic state without undo catabolism is accomplished by the systems and methods disclosed herein. It was discovered that the *S. cerevisiae* is able to stabilize the biochemical nutrients that are not anabolized by the yeast to form a nutrient-broth of biochemical nutrients. Without being confined to any particular theory as to the mechanism, it was discovered that in the presence of *S. cerevisiae* under aerobic conditions, the extracted biochemical nutrients do not putrefy, rot, or stink. Unlike the disposal of food scraps as garbage, which will begin to catabolize, and as a consequence, rot and stink within hours of disposal, the extracted biochemical nutrients held in the nutrient-rich broth can be stabilized for several weeks without any observable signs of rot or putrification. For example, in one embodiment the aerated mixture of biochemical nutrients and yeast can be held without significant catabolism of the biochemical nutrients for up to at least about 1 month, at least about 3 weeks, at least about 2 weeks. The aerated mixture of biochemical nutrients and yeast can be held for up to, for example, at least about 13 days; at least about 12 days; at least about 12 days; at least about 11 days; at least about 10 days; at least about 9 days; at least about 8 days; at least about 7 days; at least about 6 days; at least about 5 days; at least about 4 days; at least about 3 days; at least about 2 days; or least for 1 day.

The yeast, under the appropriate aerobic conditions, acts as a competitor to other microorganisms for the limiting biochemical nutrients such as simple sugars. Without being limited to a theory of the actual underlying biological manifestations, without the competition of the yeast, other microorganisms would catabolize the biochemical, resulting putrification (putrefaction) and rot of the biochemical nutrients. Under the appropriate aerobic conditions, the yeast is able to competitively take up and anabolize or stabilize the biochemical nutrients that would otherwise be available to the other catabolizing microorganisms. In this manner, the yeast is able to suppress the growth of the catabolizing microorganisms by limiting the available biochemical nutrients.

In one embodiment, it has been observed that the aerated mixture of biochemical nutrients and the yeast can be maintained for at least 7-10 days without signs of putrification, such as foul odor, thus indicating that the biochemical nutrients are stabilized. It has also been observed that the number of yeast can increase 100 fold over a 7-10 day time period, with a two-fold increase in biomass (dry weight) of individual organisms, thus suggesting that a portion of the biochemical nutrients are anabolized.

As disclosed herein, the aerated mixture of slurry and yeast can result in the preservation of the biochemical nutrients through both anabolization and stabilization of the nutrients in a nutrient-rich broth. It certain embodiments, the amount of biochemical nutrients preserved can anabolization or stabilization can vary. It is to be understood that some amount of the extracted biochemical nutrients may be lost to $CO_2$ production as a natural result of yeast respiration. Such loss is to be expected given the maintenance or eventual growth of the yeast biomass. Such loss is distinguishable from the uncontrolled loss of $CO_2$ and biomass resulting from putrification.

The amount of biochemical nutrients stabilized versus the amount of biochemical nutrients anabolized can vary. In one embodiment, the majority of the biochemical nutrients are stabilized in the nutrient-rich broth. The percentage of the biochemical nutrients stabilized in the nutrient-rich broth versus anabolized by the yeast can be, for example, greater than approximately 85%; can be greater than approximately 75%; can be greater than approximately 60%; can be greater than approximately 50%. That is, in certain embodiments, the percentage of the nutrient-rich broth that is anabolized versus stabilized can be less than approximately 15%; less than approximately 25%; less than approximately 40%; can be less than approximately 50%.

In certain embodiments, the percentage of the total amount of biochemical nutrients that are stabilized can be, for example, greater than approximately 85% of the total mass; can be greater than approximately 75% of the total mass; can be greater than approximately 60% of the total mass; can be greater than approximately 50% of the total mass. In certain embodiments, the percentage of total amount of biochemical nutrients that are anabolized can be, for example, less than approximately 15%; can be less than approximately 25%; can be less than approximately 40%; can be less than approximately 50%.

FIG. 4 is a flow diagram representing one example of a method 410 for determining the water amount and comminution duration for extracting the biochemical nutrient content of food scraps into a slurry. As illustrated in FIG. 4, method 410 may include one or more functions, operations, or actions as illustrated by one or more operations 412-420. Operations 412-420 may include the "Receiving Food Scraps" operation 412, "Weighing Food Scraps" operation 414, "Determining Food Category" operation 416, "Determining Water Amount" operation 418, and "Determining Comminution Duration" operation 420. As discussed below, the method 410 shown in FIG. 4 can be complementary to the operations performed in method 210 of FIG. 2.

In FIG. 4, operations 412-420 are illustrated as being performed sequentially, with operation 412 performed first and operation 420 performed last, and operations 414 and 416 being performed concurrently. It will be appreciated, however, that some operations may be re-ordered as convenient to suit particular embodiments, and that some operations may be performed concurrently in some embodiments. It will also be appreciated that some operations are optional to the successful completion of method 410.

Method 410 may begin at operation 412, "Receiving Food Scraps." Operation 412 can correspond to operation 212 of method 210 in FIG. 2. In operation 412, food scraps are received for processing. The food scraps received in operation 412 may originate from any location along the food supply chain from farm to ultimate consumer.

Operation 412 may be followed by operation 414, "Weighing the Food Scraps." In operation 414, the food scraps received in operation 412 are weighed to determine the weight of the food scraps received. The food scraps can be weighed in a variety of ways. In one embodiment, the food scraps can be weighed directly on a weighing device, such as a scale. In another embodiment, the relative weight of the food scraps can be determined by measuring the tare weight of the unit receiving the food weight and a gross weight of the unit after the food scraps are received. In this manner, the weight of the food scraps is calculated as the difference between the gross weight and the tare weight of the unit receiving the food scraps. In one non-limiting example, the gross weight and tare weight of the unit receiving the food scraps can be measured using one or more load cells located in the unit.

The amount of the food scraps received as part of many of the methods described herein can vary depending on the structure and equipment used in the system for processing the food scraps. In one embodiment, a minimum amount of food scraps is required for the operation of the disclosed methods. In one embodiment, a maximum amount of food scraps is set for the operation of the disclosed methods. Measuring the weight of the food scraps in operation 414 provides a way to determine whether any upper or lower limits on the amount (e.g., weight) of the food have been reached.

Operation 412 may also be followed by operation 416, "Determining a Food Category." In one embodiment, the category of the food scraps may be a conceptualization of shared characteristics of the food scraps, such as the origin of the food scraps or the primary chemical composition of the food scraps. In one embodiment, the food category can be dynamically provisioned such that the category information may be based on a particular user, premises, time of day, or based on an initial set of user responses. For example, system interface can generate a number of hierarchical based displays that collect more detailed food category information based an initial set of category selections by the user. In one embodiment, the food category of the food scraps can be dynamically determined based on real-time analysis of the food scraps when the food scraps are received. For example, the category of the food scraps may be based on analysis of electromagnetic data (e.g., light absorbance or reflectance and color differences such as wavelength shifts), smell data, temperature data, etc.

In another embodiment, the determination of the food category of the food scraps may be based on selection of the category from a static list of available categories. For example, when the food scraps are received from a grocery store, the food categories may be based on the originating location (e.g., food department) of the food scraps in the grocery store, such as the meat department or the delicatessen. In one non-limiting example, the food categories can be selected from meat and seafood, delicatessen, grocery, prepared foods, produce, juice and coffee bar, floral, and bakery.

Determination of the food category can be based on the chemical composition of the food scraps. For example, starch-based foods may be considered a food category or protein-based foods may be considered a food category. In one embodiment, the food scraps received by method 410 may always be of a certain category (for example, if the system is located at a dairy farm and milk is the only food category), so the food category of the food scraps may be fixed in method 410 according to the category of food always received.

Operation 414 and/or 416 may be followed by operation 418, "Determining the Water Amount." Based on the weight of the food scraps and the food category, as a reflection of the biochemical nature of the foods in the category, the water amount needed for comminution of the food scraps received may be determined in operation 418. Instead of using a fixed quantity of water for all food weights and categories, the relative amount of water mixed with the food scraps can be selected to produce consistent characteristics of the slurry (e.g., particle size and slurry consistency) following comminution, regardless of the food category or food weight. Using a variable amount of water based on the food category and weight can also conserve water, in contrast to using a fixed amount of water for comminution, which may oversupply the water for certain food categories or quantities of food scraps.

Operation 418 may be followed by operation 420, "Determining Comminution Duration." In some embodiments, operations 418 and 420 may be performed concurrently. In some embodiments, operation 420 may be performed prior to operation 418. The average duration for comminuting the food scraps may vary, and can be based on the weight of the food scraps and the food category. Establishing the comminution duration needed for the particular food weight and category can be advantageous for comminuting the food scraps to the desired particle size. Using a fixed comminution duration for any and all food weights and categories could leave some food scraps under comminuted and produce larger than desirable food particles, thus not allowing all biochemical nutrients to be extracted from the food scraps. Furthermore, using a variable comminution duration based on food weight and category can conserve energy because the comminution device would not be operating longer than necessary. This is in contrast to using a fixed comminution duration, which may require the comminution device to be operated for an excessive duration in an attempt to fully comminute the food scraps.

In some embodiments, the average duration for comminuting the food scraps can be in the range of about 30 seconds to about 180 seconds. For example, the average time period for comminuting the food scraps can be about 30 seconds, about 40 seconds, about 50 seconds, about 60 seconds, about 70 seconds, about 80 seconds, about 90 seconds, about 100 seconds, about 110 seconds, about 120 seconds, about 160 seconds, or any range including any two of these values.

Some embodiments disclosed herein include a system configured to perform one or more methods or operations disclosed. FIGS. 5A-5D are block diagrams illustrating examples of a system for extracting the biochemical nutrients from organic material, such as food scraps, and stabilizing and/or anabolizing the extracted biochemical nutrients. FIG. 5E is a schematic diagram of a system for extracting the biochemical nutrients from food scraps and stabilizing and/or anabolizing the extracted biochemical nutrients. The systems shown in FIGS. 5A-5E contain multiple components for conducting the operations and methods described above and it will be appreciated by one of skill in the art that the components are not limited to the arrangements shown in the figures, but can be arranged in alternative arrangements to accomplish the operations and methods disclosed.

Figure 5A:
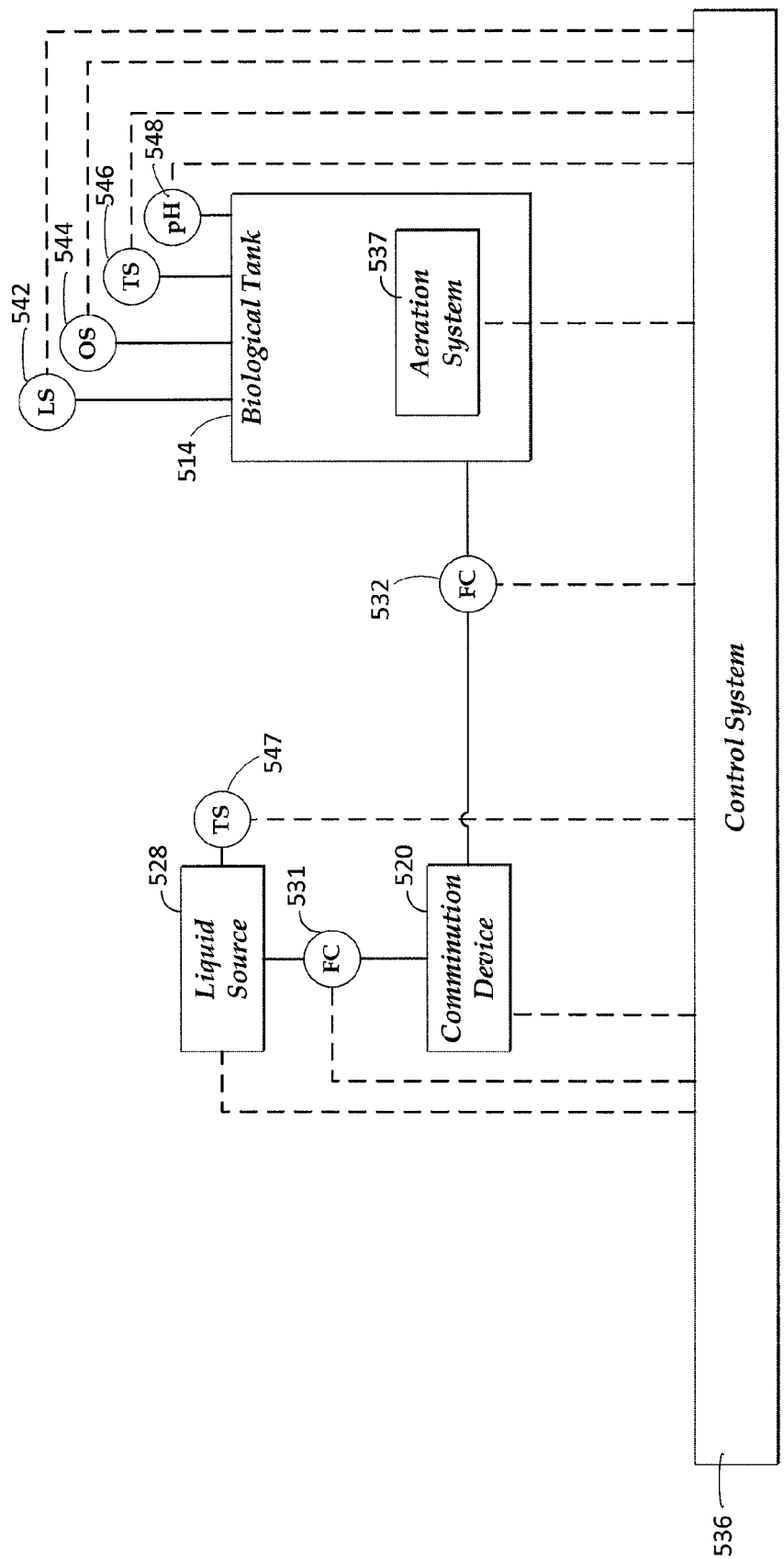
FIG. 5A is a block diagram illustrating one example of a system for extracting the biochemical nutrients from organic material and stabilizing and/or anabolizing the biochemical nutrients.

FIG. 5A is a block diagram illustrating one example of a system for extracting the biochemical nutrients from organic material and stabilizing and/or anabolizing the biochemical nutrients. The system 510 may include such components as a control system 536, a liquid source 528, a flow control device 531, a comminution device 520, a flow control device 532, a biological tank 514, an aeration system 537, and one or more sensors.

As shown in FIG. 5A, the control system 536 may be in communication with the components of system 510. As used herein, "in communication" can include any configuration that permits one- or two-directional exchange of signals (e.g., data, instructions, etc.) between two components. Two components may exchange signals, for example, via a wired connection, wirelessly, or through access to shared memory (e.g., flash memory). The exchange may occur through an intermediate device, such as a separate controller.

In some embodiments, the control system 536 may be coupled to a communication device (not shown) for communicating with a remote system or user. The communication device is not particularly limited and can be, for example, a narrow (data) or wide band (video) cellular modem, a landline modem, a wifi device, and ethernet modem, and the like. Control system 536 may send data for system 510 via the communication device to a remote site or user. For example, the control system 536 may send error reports when one or more operating conditions are outside acceptable thresholds. In some embodiments, a user can remotely configure or control system 510 by sending signals to control system 536 via the communication device.

While the control system 536 is depicted in FIG. 5A as implemented by a single computing device, this is illustrative only. The control system 536 may be embodied in a plurality of linked computing devices. A server or other computing device implementing the control system 536 may include memory, processing unit(s), and computer readable medium drive(s), all of which may communicate with one another by way of a communication bus. The processing unit(s) may communicate to and from memory containing program instructions that the processing unit(s) executes in order to operate the control system 536. The memory generally includes RAM, ROM, and/or other persistent and auxiliary memory.

The control system 536 can include an external data source interface component for obtaining external information from network data sources, such as location data, contact data, inventory data, and other data. The control system 536 can also include a device interface component for obtaining information from one or more system interfaces 524. One skilled in the relevant art will also appreciate that the control system 536 may include any one of a number of additional hardware and software components that would be utilized in the illustrative computerized network environment to carry out the illustrative functions of the control system 536 or any of the individually identified components. The control system 536 may also include one or more input devices (keyboard, keypads, mouse device, specialized selection keys, multi-media capture devices, barcode readers, RFID receivers, etc.) and one or more output devices (displays, printers, audio output mechanisms, etc.).

The comminution device 520 may receive organic material and may comminute the organic material into a slurry. The comminution device 520 may be in communication with control system 536. The control system 536 may, for example, receive signals from comminution device 520 indicating when the organic material has been received. The control system 536 may send signals to the comminution device instructing the comminution device 520 to operate. The operation instructions from the control system 536 to the comminution device 520 may include a duration for how long the comminution device 520 should operation. The control system 536 may receive signals from the comminution device 520 indicating when the organic material has been comminuted.

The control system 536 may provide liquids from the liquid source 528 (e.g., a municipal water line or water tank) to the comminution device 520, to which the liquid source 528 may be fluidly coupled. The flow control device 531 may be in communication with the control system 536 to adjust the amount of water added when forming the slurry. As used herein, a "flow control device" can include a pump or valve and optionally other components (e.g., volumetric sensors and weighing devices) that, when in communication with a control system, can control the quantity of material transferred between two components. Thus, in some embodiments, the control system 536 may be configured to form a slurry according to any of the methods described above (e.g., control the slurry composition as described for operation 216 in FIG. 2). The liquid source 528 may include a temperature sensor 547 which may be in communication with the control system 536 to regulate the temperature of liquid supplied to the comminution system 520.

The flow control device 532 may be in communication with the control system 536 and may be located downstream of the comminution device 520. The flow control device 532 may be configured to adjust a flow of organic components, such as the slurry, from the comminution device 520 to the biological tank 514. For example, control system 536 may signal flow control device 532 to provide organic material to the biological tank 514 when the comminution device 520 has stopped operation.

The biological tank 514 may contain a yeast in solution. The biological tank 514 may receive a slurry, such as, for example, the slurry produced in the comminution device 520. The slurry and the yeast may form a mixture in the biological tank 514. The biological tank 514 may include an aeration system 537. The aeration system 537 may be in comminution with the control system 536 to supply an amount of oxygen to the mixture in the biological tank 514. The yeast can stabilize or anabolize the biochemical nutrients in the mixture in the biological tank 514 under aerobic conditions (e.g., as described above with relation to operations 318 and 320 in FIG. 3).

The biological tank 514 may also include various components for sensing various conditions of the mixture. The level sensor 542, oxygen sensor 544, temperature sensor 546, and pH sensor 548, are configured to sense various characteristics of the biological tank 514. Each of these sensors may be in communication with control system 536, which can receive data regarding the mixture and make appropriate adjustments to the process. For example, if level sensor 542 indicates the biological tank 514 is full, the control system 536 may stop providing slurry to the biological tank 514 using the flow control device 532. As another example, the control system 536 may receive temperature conditions from temperature sensor 546. As another example, the control system 536 may be in communication with the pH sensor 548. As another example, the control system 536 may be in communication with the oxygen sensor 544 and can adjust the operation of the aeration system 537 to provide more or less aeration of the mixture in the biological tank 514 as required. Thus, in some embodiments, the control system 536 may be configured to aerate the mixture according to any of the methods described above (e.g., control the oxygen content of the mixture as described for operation 316 in FIG. 3).

Figure 5B:
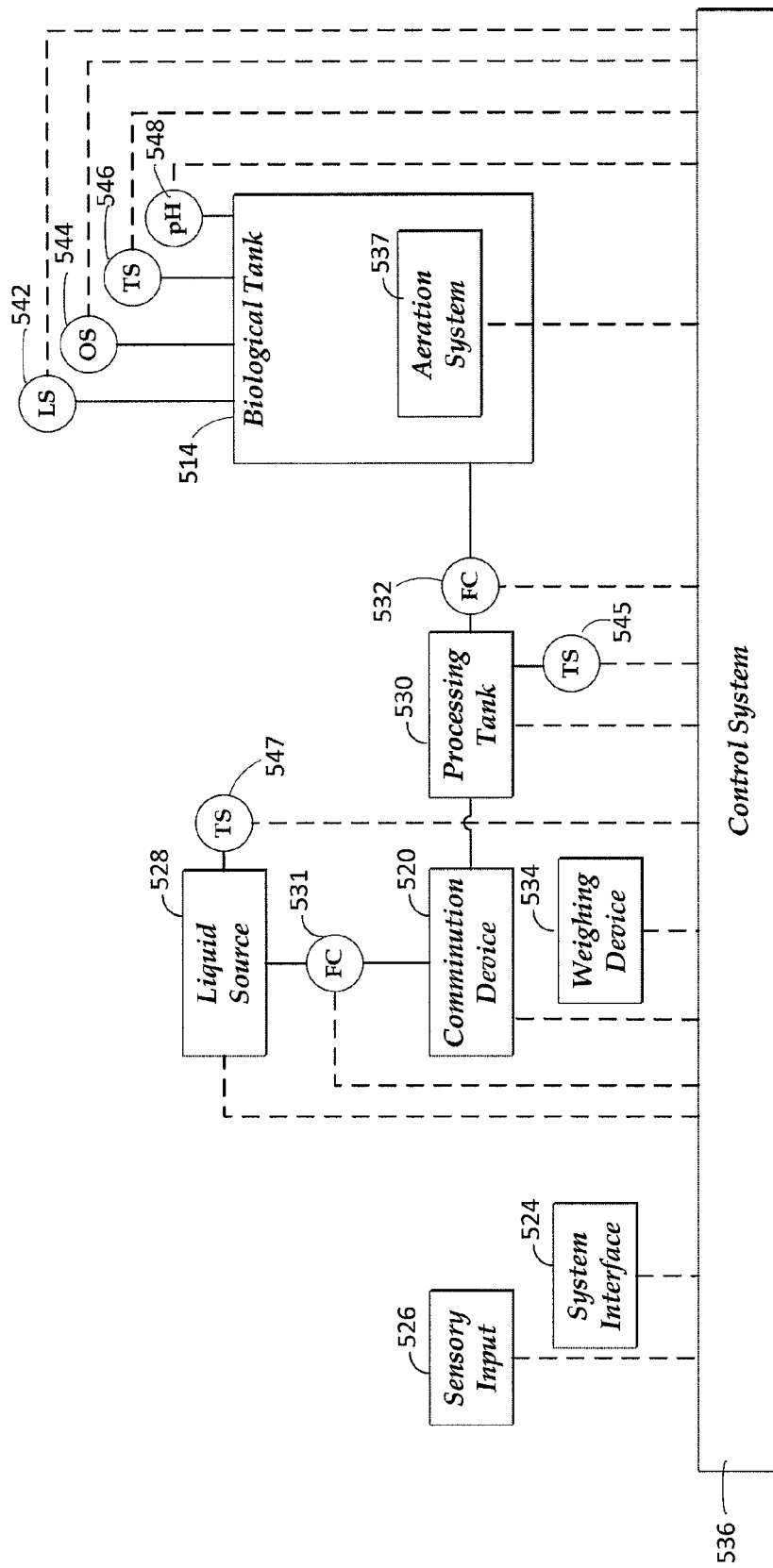
FIG. 5B is a block diagram illustrating one example of a system for extracting the biochemical nutrients from organic material and stabilizing and/or anabolizing the biochemical nutrients.

FIG. 5B is a block diagram illustrating one example of a system for extracting the biochemical nutrients from organic material and stabilizing or anabolizing the biochemical nutrients. Shown in FIG. 5B is the system 510 having the same components as system 510 of FIG. 5A and further including a sensory input device 526, a system interface 524, a weighing device 534, and a processing tank 530, all of which are in communication with the control system 536.

The weighing device 534 may be configured to receive the amount of organic material provided to the system for processing. The weighing device 534 may also be configured to weigh components of the system 510 before and after the organic material is received. The control system 536 may determine an appropriate amount of liquid to combine with organic material based, in part, on data received from the weighing device 534 (e.g., as described above with respect to operation 418 in FIG. 4). The control system may also determine an appropriate comminution duration for the organic material based, in part, on data received from weighing device 534 (e.g., as described above with respect to operation 420 in FIG. 4).

The system interface 524 shown in FIG. 5B may receive input data from a user of the system and transmit such data to the control system 536. The system interface 524 can include various input and output devices for generating information, prompting a user for information, obtaining user inputted information and initiating the processing of received organic material. One of skill in the art will appreciate, however, that additional or alternative displays may be implemented in accordance with the present disclosure. Likewise, the system interface 524 may receive data from the control system 524 related to any function of the system 510 and display the data or related information on the system interface 524. All data received by the control system 536 from the system components may be transmitted to the system interface 524 for display. Control system 536 may also be configured to receive information from outside the system 510 illustrated by FIG. 5B. It should appreciated that a user can send information to the control system 536, including such information as weight, category, or type of organic material, and the like, prior to arrival of the material at the system 510.

The control system 536 may determine an appropriate amount of liquid to combine with organic material based, in part, on data received from the system interface 524 (e.g., as described above with respect to operation 418 in FIG. 4). The control system 536 may also determine an appropriate comminution duration for the organic material based, in part, on data received from the system interface 524 (e.g., as described above with respect to operation 420 in FIG. 4). In one embodiment, the system interface 524 may receive data from a user regarding the category of the organic material received in the system 510.

The sensory input device 526 shown in FIG. 5B may receive environmental input data and transmit such data to the control system 536. The environmental input data can be stored as data by or in the control system 536. The sensory input device 526 may receive, for example, the wavelength of electromagnetic radiation emitted from the organic material. In another example, the sensory input device 526 may receive light data, color data, sound data, temperature data, smell data or other characteristic data of the organic material.

The control system 536 may determine an appropriate amount of liquid to combine with organic material based, in part, on data received from the sensory input device 526 (e.g., as described above with respect to operation 418 in FIG. 4). The control system 536 may also determine an appropriate comminution duration for the organic material based, in part, on data received from the sensory input device 526 (e.g., as described above with respect to operation 420 in FIG. 4). In one embodiment, the sensory input device 526 may receive data regarding the category of the organic material received in the system 510.

System 510 may further include a processing tank 530, such as, for example, a hydrolytic tank. The processing tank 530 may be fluidly coupled with the comminution device 520 and may receive the slurry after the organic material is comminuted for further processing of the slurry prior to delivery of the slurry to the biological tank 514. The processing tank 530 may be fluidly coupled to the biological tank 514. The control system 536 may provide instructions to provide hydrolytic enzymes to the processing tank 530 (e.g., as described above with respect to operation 218 in FIG. 2). The control system 536 may provide instructions to heat the processing tank 530 to pasteurize the slurry (e.g., as described above with respect to operation 220 in FIG. 2). The flow control device 532 may be in communication with the control system 536 and configured to adjust a flow of the slurry from the processing tank 530 to the biological tank 514. The processing tank 530 may include a temperature sensor 545 which may be in communication with the control system 536 to regulate the temperature of the processing tank 530.

Figure 5C:
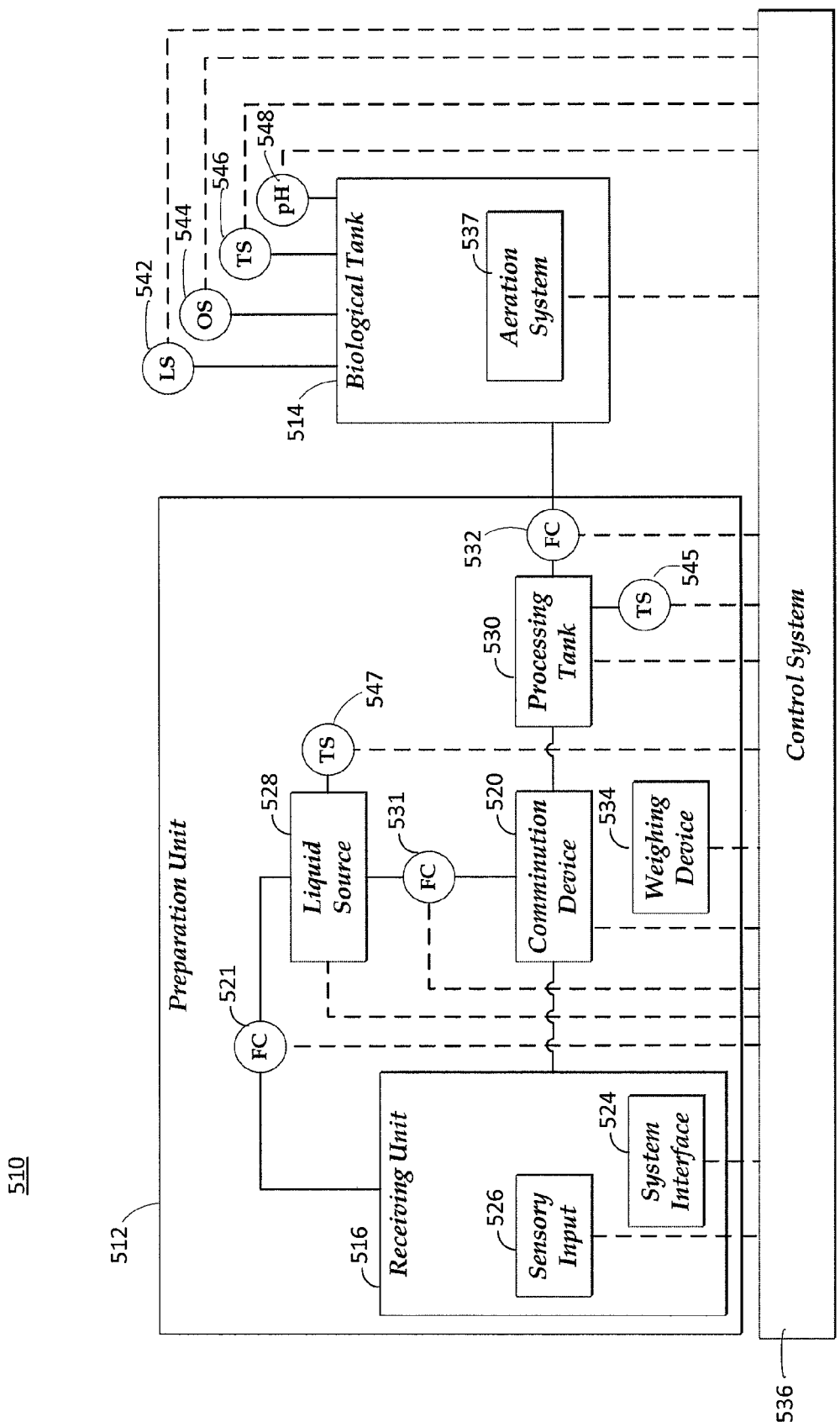
FIG. 5C is a block diagram illustrating one example of a system for extracting the biochemical nutrients from organic material and stabilizing and/or anabolizing the biochemical nutrients.

FIG. 5C is a block diagram illustrating one example of a system for extracting the biochemical nutrients from organic material and stabilizing or anabolizing the biochemical nutrients. Shown in FIG. 5C is system 510 having the same components as system 510 and further including a receiving unit 516, a preparation unit 512, and a flow control device 521 in communication with the control system 536.

The receiving unit 516 can be, for example, a hopper, a chute, a container, or the like. The receiving unit 516 may be configured to receive the organic material and may be fluidly coupled to the comminution device 520. When organic material is received in the receiving unit 516, it can be passed through to the comminution device 520 for comminution and extraction of the biochemical nutrients. In one embodiment, the receiving unit 516 may comprise the sensory input device 526 or the system interface 524. In one embodiment, the receiving unit 516 may be fluidly coupled with the liquid source 528. The control system 536 may supply an amount of water to the receiving unit 516 to assist in comminution of the organic material, to clean the receiving unit 516, etc. The temperature sensor 547 which may be in communication with the control system 536 to regulate the temperature of liquid supplied to the receiving unit 516. The flow control device 521 may be in communication with the control system 536 to adjust the amount of water supplied to the receiving unit 516. Furthermore, the control system 536 may provide signals to flow control devices 521 and 531 to variably allocate the amount of water supplied to the receiving unit 516 and the comminution device 520 based on data received by the control system 536 from other components of the system, such as the weighing device 534, the sensory input device 526, the comminution device 520, or any combination thereof.

The preparation unit 512 may be an assembly or aggregation of one or more components of the systems described herein. In one embodiment, the preparation unit 512 may be a structure with a closed interior portion configured to house one or more components of the systems described herein. In one embodiment, the preparation unit 512 may house any combination of the receiving unit 516, the liquid source 528, the comminution device 520, the weighing device 534, the processing tank 530, and one or more flow control devices. In one embodiment, the preparation unit 512 may house the control system 536.

Figure 5D:
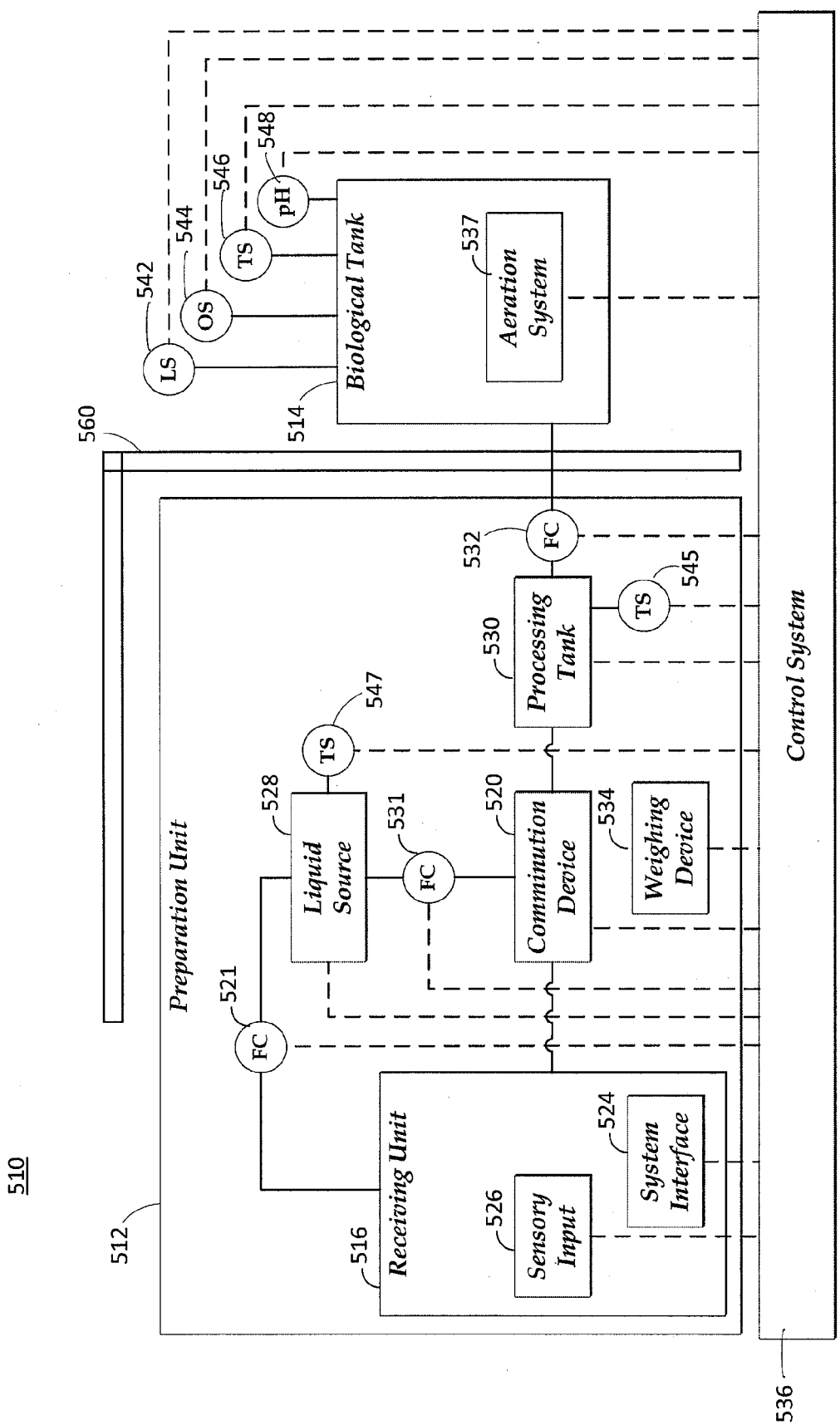
FIG. 5D is a block diagram illustrating one example of a system for extracting the biochemical nutrients from organic material and stabilizing and/or anabolizing the biochemical nutrients.
Figure 5E:
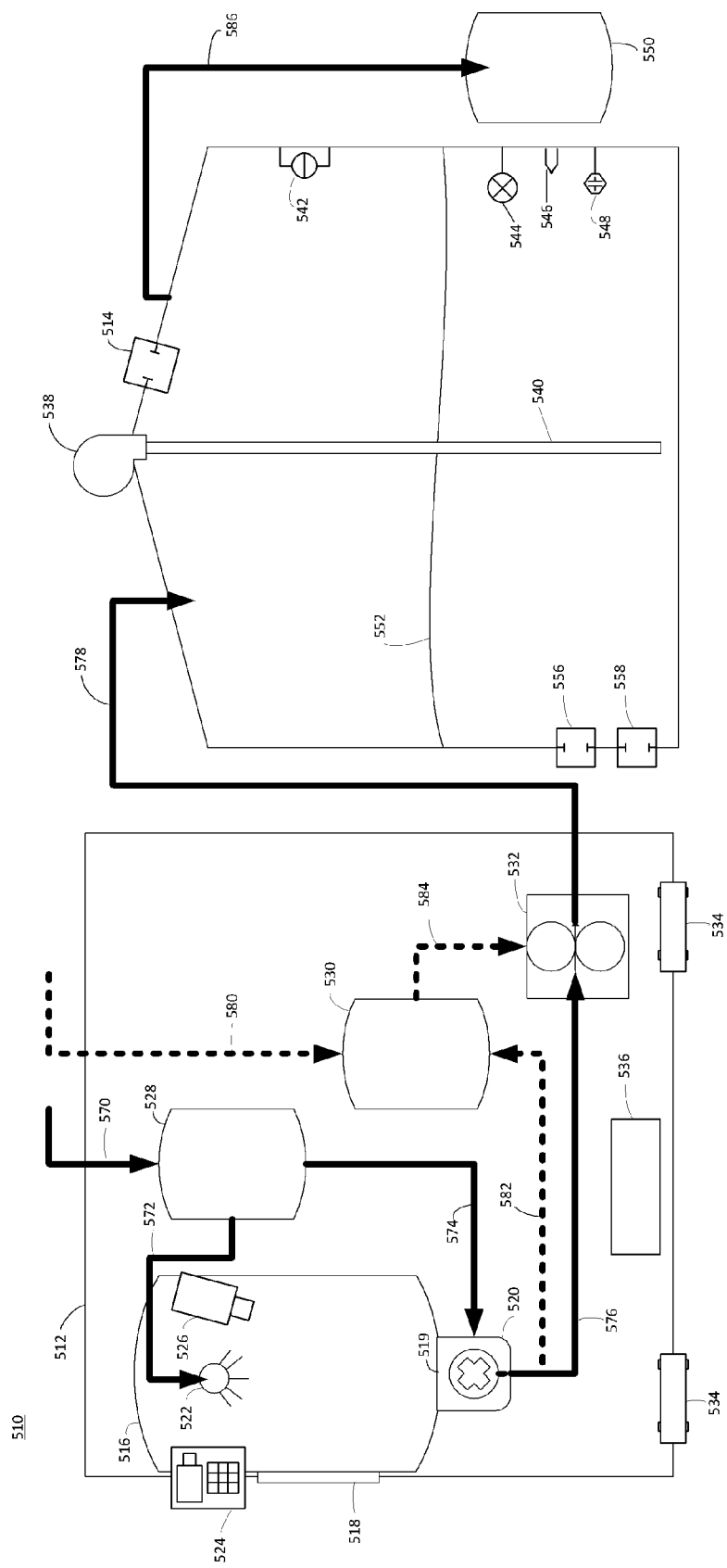
FIG. 5E is a schematic diagram illustrating one example of a system for extracting the biochemical nutrients from organic material and stabilizing and/or anabolizing the biochemical nutrients.

FIG. 5D is a block diagram illustrating one example of a system for extracting the biochemical nutrients from organic material and stabilizing and/or anabolizing the biochemical nutrients. As shown in FIG. 5D, the preparation unit 512 may be located in an edifice 560 (e.g., a grocery store, warehouse, residence, etc.) and the biological tank 514 may be located outside the edifice 560. In this manner, the organic material may be received by the system 510 while in the edifice 560 and the biochemical nutrients may be extracted while in the edifice 560, but the biochemical nutrients may be stabilized and/or anabolized outside the edifice 560. It will be readily appreciated by one of skill in the art that various components of the preparation unit 512 may be removed from the preparation unit 512 and moved out of the edifice 560. For example, in one embodiment, the components of the system 510 may be arranged such that the organic material may be received in the edifice 560, but the biochemical nutrients may be extracted and stabilized and/or anabolized outside the edifice 560.

FIG. 5E is a schematic diagram illustrating one example of system for extracting biochemical nutrients from organic material, particularly food scraps, and anabolizing and/or stabilizing the biochemical nutrients, as depicted in FIG. 1. The system 510 may include a preparation unit 512 where the biochemical nutrients can be extracted from the food scraps. The system 510 can also include a biological tank 514 where the extracted biochemical nutrients can be stabilized or anabolized. The preparation unit 512 can include several components, including a receiving unit (e.g., a hopper) 516, a comminution device 520, a pump 532, a water tank 528, a control system 536, a system interface 524, and one or more weighing devices 534 and conveying devices (not shown) that serve to deliver food scraps at a constant rate to the comminution device 520. Shown in FIG. 5E is an optional hydrolytic tank 530 that may be included in the preparation unit 512 to hydrolyze and pasteurize the slurry prior to anabolization and stabilization, as discussed above. The hopper 516 can include several components, such as an inlet 518, an outlet 519, a spray nozzle 522, and a camera 526. The preparation unit 512 may be used, for example, to perform operation 114 in system 110 of FIG. 1, and all or part of the operations depicted in system 210 of FIG. 2, for extracting biochemical nutrients from the food scraps. The preparation unit 512 may also be used, for example, to perform all or part of the operations depicted in system 410 of FIG. 4 for determining the water quantity for comminution and the comminution duration.

The control system 536 can be in communication with the components and any subcomponents of the preparation unit 512 and the biological tank 514. In one embodiment of system 510, such as is shown in FIG. 5E, the control system 536 may be a component of the preparation unit 512. In another embodiment, the control system 536 may be located external to the preparation unit 512, but remain in communication with the preparation unit 512, the biological tank 514, and the components and subcomponents of each.

The biological tank 514 can include a number of components, including an aeration system. In one embodiment, such as is depicted in FIG. 5E, the aeration system can be comprised of a regenerative blower 538 in communication with a bubbler 540. Other aeration systems are contemplated within the scope of the disclosure provided herein, such as, for example, venturi pump connected to the bubbler 540. The biological tank 514 can further include a top port 554, a first drainage port 556, a second drainage port 558 and a number of sensors, such as a level sensor 542, a pH sensor 544, a temperature sensor 546, and a dissolved oxygen sensor 548. As shown in FIG. 5E, the biological tank may be connected to a charcoal tank 550. The biological tank 514 may be used, for example, to perform operations 116 and 118 in system 110 depicted in FIG. 1, and all or part of the operations depicted in system 310 of FIG. 3, for anabolizing and stabilizing the biochemical nutrients in the slurry.

In one embodiment of the system 510 shown in FIG. 5E, the hopper 112 receives a quantity of food scraps. The hopper 516 may be used, for example, to perform all or part of operations 112, 212, and 412 depicted in FIGS. 1, 2, and 4, respectively. As discussed above, the food scraps can originate at any location along the food supply chain. For example, the food scraps can be the unwanted or left over food scraps or other organic material (e.g., flowers, house plants, etc.) collected in a grocery store or in a residence. A user of the system 510 may deposit the food scraps into the hopper 516 through the inlet 518.

The system 510 can include a system interface 524 in communication with the control system 536. In one embodiment, the system interface 524 is a component of the preparation unit 512.

Using the system interface 524, the user may provide to the control system 536, the category of food scraps being deposited into the hopper 516. For example, the user may select from a number of predefined food categories shown on the system interface 524 in order to indicate the category of food scraps being deposited into the hopper 112. Alternatively, in one embodiment, the system 510 may determine the food category deposited into the hopper 516 with little or no user involvement. For example, the camera 526 can be a multispectral camera capable of determining the food type based on, for example, the wavelength of electromagnetic radiation emitted from the food scraps. In another example, the preparation unit 512 can include additional sensors, such as light sensors, color sensors, sound sensors, temperature sensors, smell sensors, etc. that collect information about characteristics of the deposited food scraps. The food category can be stored as data by or in the control system 536.

The control system 536 may determine an appropriate amount of water to combine with the food scraps based, in part, on data received from the weighing device 534 and the system interface 524 or camera 526 (e.g., as described above with respect to method 410 in FIG. 4). Thus, the system interface 524 and control system 536 may be used, for example, to perform all or part of operation 416 depicted in FIG. 4. Likewise, the camera 526 and control system 536 can be used, for example, to perform all or part of operation 416 depicted in FIG. 4. In turn, the control system 536 may communicate with the water tank 528, thus providing instructions to the water tank 528 to supply the appropriate amount of water to the comminution device 520 and hopper 516.

With the food scraps having been received in the hopper 516, the food scraps can be weighed. The weighing device 534 can be in communication with the control system 536. In one embodiment, the weighing device 534 can weigh the food scraps directly and communicate the weight of the food scraps directly to the control system 536. The weighing device 534 may be used, for example, to perform all or part of operation 414 depicted in FIG. 4.

In one embodiment, the weighing device 534 is comprised of one or more load cells. In this embodiment, the weight of the received food scraps can be determined by the use of one or more load cells, as part of the preparation unit 512. The load cells can determine the tare weight of the preparation unit 512 before any food scraps have been received in the hopper 516. Following receipt of the food scraps in the hopper 516, the load cells are able to measure the gross weight of the preparation unit 512 and the food scraps. The control system 536, in communication with the load cells, can determine the net weight of the food scraps added to the hopper 516 based on the difference between the gross weight of the preparation unit 512 and food scraps and the tare weight of the preparation unit 512. Thus, the load cells and control system 536 may be used, for example, to perform all or part of operation 414 depicted in FIG. 4. In one non-limiting embodiment, with the assistance of logic in the control system 536, excess net weight in the comminution device 520 following the completion of a cycle could be detected and a new comminution cycle started and timed based on the residual, unprocessed food scraps. Similarly, the combination of load cell and optical data could detect the presence of unwanted, non-processable or contaminant (where a contaminant is a non-recyclable/non-recoverable object such as a stone) material in the hopper or comminution device 520. In another embodiment, the weighing device 534 may be a scale positioned externally to the preparation unit 512 and in communication (wired or wirelessly) with the control system 536.

As shown in FIG. 5E, the hopper 516 can be coupled to a comminution device 520. For example, the hopper 516 may include an outlet 519 that couples to the comminution device 520. In one embodiment, the outlet 519 is through a bottom portion of the hopper 516 and provides a passage to the comminution device 520. In this embodiment, the food scraps received by the hopper 516 can pass through the hopper outlet 519 to enter the comminution device 520. In another embodiment, the hopper may be fluidly coupled to the comminution device via one or more conduits (not shown). The comminution device 520 can be, for example, a grinder, homogenizer, crusher, a mill, rotating blade(s), and the like, so long as the device results in the desired size, shear forces and other characteristics.

The comminution device 520 and the hopper 516 can be fluidly coupled to the water tank 528. As used herein, "fluidly coupled" can include any connection through one or more conduits than allows the exchange of material between two components. Two components may be fluidly coupled when one or more intermediate components receive or process a fluid that is transferred between the two components. The water tank 528 can be, for example, a hot water heater. The water tank 528 may be a water heater capable of providing hot water to the hopper 516 and comminution device 520 to assist in the grinding of the food scraps. In one example, the temperature of the water supplied from the water tank 528 to the hopper 516 and comminution device 520 can be between ambient temperature and approximately 140° F. The water tank 528 can be fluidly coupled to an external water supply through conduit 570. In another embodiment, the water tank 528 can be absent from the system 510 and the water can be supplied directly to the comminution device 520 and the hopper 516 from the external water supply (such as a municipal water source or external water tank).

The water tank 528 can supply water or other fluid to the comminution device 520 and hopper 516 to assist in and enhance the comminution of the food scraps. In one embodiment, the water tank 528 is fluidly coupled through conduit 572 to the spray nozzle 522, such that the spray nozzle 522 sprays the water into the hopper 516. As used herein, "conduit" can include a pipe or tube or other means to fluidly connect the respective components. The spray nozzle 522 may be located in an interior region of the hopper 516, for example, above the hopper outlet 519. As the hopper outlet 519 may be coupled with the comminution device 520, approximately all the water supplied to the hopper 516 through the spray nozzle 522 can flow down to the comminution device 520. In one embodiment, the water tank 528 is fluidly coupled to the comminution device 520 through a conduit 574. After the amount of water required for comminution has been determined based on, for example, the weight of the food scraps and the food category, the correct water quantity can be supplied to the spray nozzle 522 and comminution device 520. The determined amount of water needed for successful comminution can be variably distributed between the spray nozzle 522 and the comminution device 520 (from 16% of the water flow to 100%). Water supplied to each site can be either at ambient or heated between 140° F. and 180° F. Furthermore, the determined amount of water needed for comminution can be variably distributed to the spray nozzle 522 and the comminution device 520 at different times. For example an amount of water may be supplied to the nozzle 522 and the comminution device before comminution commences, an amount of water may be supplied during comminution, and an amount of water may be supplied after comminution. In one embodiment, an amount of water may be sprayed through the nozzle 522 after the comminution device has finished running in order to clear any remaining food particles from the hopper 516.

The comminution device 520 may be operated for a specific period of time in order to form a slurry containing biochemical nutrients extracted from the food scraps and generate food particulates of a desired size in the slurry. The comminution device 520 may be used, for example, to perform all or part of operation 216 depicted in FIG. 2. As discussed above, the comminution duration needed for the desired particulate size in the comminution device 520 can be a function of the food category of the food scraps and/or the weight of the food scraps added to the hopper 516. The food category and weight of the food scraps can be stored as data in the control system 536 and the control system 536 can determine the appropriate duration of comminution for the comminution device 536. In turn, the control system 536 may communicate with the comminution device 520, thus providing instructions to the comminution device 520 to operate for the determined duration. In one embodiment such control allows the comminution device 520 to be used to move the food scrap slurry to fluidly connected pump 532.

The food scraps can be sufficiently comminuted to expose the surface area of the food particles by the shear force of the comminution device 520 in order to shear or lyse all or nearly all available cells in food particles. The slurry produced in the comminution device 520 can be pumped via the pump 532 to the biological tank 514 via conduit 578. The pump 532 can be, for example, a reciprocating pump, a rotary pump, a centrifugal pump, a lobe pump, or the like. In one embodiment, the pump 532 can be fluidly coupled to the comminution device 520 through conduit 576. In one embodiment, the pump 532 can be directly coupled to the comminution device 520.

In one alternative embodiment, the slurry may first pass through conduit 582 to the hydrolytic tank 530 prior to being pumped to the biological tank 514. In the hydrolytic tank 530, the slurry can undergo hydrolysis and/or pasteurization. The hydrolytic tank 530 can be fluidly coupled to an internal or external tank though conduit 580 to receive a solution of hydrolytic enzymes needed for hydrolysis. In the hydrolytic tank 530, the slurry can be mixed with hydrolytic enzymes to assist in hydrolysis of the extracted biological nutrients. In the hydrolytic tank 530, the slurry can also be subject to heating sufficient to pasteurize the slurry. The hydrolytic tank 530 can be used, for example, to perform all or part of operations 218 and 220 depicted in FIG. 2. Following hydrolysis and/or pasteurization in the hydrolytic tank 530, the slurry can be removed from the hydrolytic tank 530 through conduit 584 and passed through the pump 532 to pump the slurry into the biological tank 514 via conduit 578.

The biological tank 514 can receive the slurry prepared in the preparation unit 512. The biological tank 514 can be used, for example, to perform all or part of operation 312 depicted in FIG. 3. In an alternative embodiment, a slurry may be received from some other process or system and provided to the biological tank 514. The biological tank 514 may contain a yeast in solution under aerobic conditions. In one embodiment, the yeast is *Saccharomyces cerevisiae*. The biological tank 104 can be equipped with an aeration system 126 to provide oxygen to the biological tank 104 in order to aerate the mixture of the slurry and the yeast. The aeration system of the biological tank may also act to mix the slurry with the yeast. Thus, biological tank and the aeration system together can be used to perform all or part of operations 314 and 316. In another embodiment, a mechanical mixer (not shown) may be used to mix the mixture of the slurry and the yeast. In one embodiment, the biological tank 514 can be, for example, an industrial food grade tank. The capacity of the biological tank can be chosen based on the volume of the slurry being received in the biological tank 514 and the frequency of the drainage and pick up of the slurry/yeast mixture for further processing. In one embodiment, the biological tank 514 can be a food-safe epoxy-coated mild steel tank with a capacity of 1000-4000 gallons. In one non-limiting example, the biological tank can have a capacity of 3500 gallons, with a working capacity of 3000 gallons.

In one embodiment, such as is shown in FIG. 5E, the aeration system may be comprised of a regenerative blower 538 fluidly coupled to a bubbler 540. The blower 538 may be located within the roof of the biological tank 514. The blower 538 may draw in ambient air from the atmosphere and force the air down through the bubbler 540 and into the slurry in the tank 514. In one embodiment, the bubbler 540 comprises a tube or pipe passing down through the slurry in the tank 514, having one or more holes or openings in bottom of the tube, located preferably near the bottom of the biological tank 514. Air received into the bubbler 540 may be forced out of the opening in the tube into the slurry. The air forced out of the bubbler may then rise, or bubble, through the slurry, thereby aerating the mixture of the slurry and the yeast. In one embodiment, the aeration system may be comprised of a venturi pump or a toring turbine located on the top of the biological tank 514 and attached to the bubbler 540 passing through the slurry. Aeration can be performed at ambient temperature and pressure in the biological tank 514.

The aeration system may be configured to aerate the slurry/yeast mixture in such a manner that the mixture is maintained in a quiescent state in the biological tank 514. In this manner, the aeration system may advantageously provide sufficient oxygen to the biological tank 514 to aerate the mixture and maintain the yeast in an aerobic environment, but not so much oxygen to feed any bacteria remaining in the slurry. Excessive aeration in the biological tank 514 may feed the bacteria (with a faster turnover rate) in the tank as well as the yeast (with a slower turnover rate) in the tank 514, causing the bacteria to overwhelm the yeast. Thus, excessive aeration may lead to foaming in the biological tank 514 as the bacteria respire in the biological tank 514. In one embodiment, the biological tank 514 may be maintained in a quiescent state by maintaining an oxygen content in the mixture of less than approximately 8 ppm, for example between approximately 0.5 ppm and approximately 8 ppm. In one embodiment, the oxygen content may be maintained at approximately 1-3 ppm to maintain the quiescent state of the mixture in the biological tank 514.

The biological tank 514 may be equipped with one or more sensors, such as a level sensor 542, a pH sensor 544, a temperature sensor 546, and an oxygen sensor 548. Such sensors may be in communication with the control system 536. The level sensor 542 may monitor the fluid level 552 in the biological tank 514 and provide feedback to the control system 536. The pH sensor 544 may monitor the pH of the mixture in the biological tank 514 and provide feedback to the control system 536. The temperature sensor 546 may monitor the temperature in the mixture in the biological tank 514 and provide feedback to the control system 536. The oxygen sensor 548 may monitor the oxygen content in the biological tank 514 and provide feedback to the control system 536. Based on the feedback received from the sensors, the control system 536 may provide instructions to components of the system 510. For example, in one embodiment the control system 536 may provide instructions to the aeration system to increase or decrease the aeration provided to the mixture in the biological tank 514 based on feedback (e.g., data) received from the oxygen sensor 548.

The biological tank 514 may also be equipped with one or more water recycling devices such as dewatering filters. Such reclaimed water from the biological tank 514 could then be fluidly coupled in a closed loop to the comminution device 520. Such recycling devices would result in reducing the amount of new water required by the comminution device 520 and under the system control 536 would allow optimal utilization of new and reclaimed water.

The biological tank 514 may be equipped with one or more drainage ports, such as a first drainage port 556 and a second drainage port 558. The drainage ports 556, 558 may allow the biological tank 514 to be drained and the slurry/yeast mixture to be removed from the biological tank 514 for further processing into, for example, plant fertilizer or other valuable agricultural products. The first drainage port 556 is located above the second drainage port 558 such that if the mixture is removed from the first drainage port 556 a quantity of the mixture may remain in the biological tank 514. Leaving a quantity of the mixture in the biological tank 514 following drainage of the biological tank 514 can prepare the biological tank 514 for the next receipt of additional slurry into the biological tank 514. The biological tank 514 may also be equipped with a top port 554. The top port 554 may be used to supply additional yeast to the biological tank 514 as needed.

The charcoal tank 550 can be fluidly coupled to the biological tank 514 through conduit 586. In one embodiment, the charcoal tank 550 may be equipped with activated charcoal granules and may be plumbed as the only air escape for the biological tank 514. The charcoal tank 550 can provide odor control to the biological tank 514.

As described above, the system 510 in certain embodiments may receive input data from the user or the system 510 may generate input data or information to further instruct processes conducted within the system 510. For example, as described above, the user of the system 510 may supply input data, or the system 510 may generate data, used by the control system 536 for determining, for example, the comminution duration of the comminution device 520 and/or the appropriate amount of water to combine with the organic material used in forming the slurry.

Furthermore, as described above, control system 536 may also be configured to receive information from outside the system 510. A user may send information to the control system 536, including such information as weight, category or type of organic material, unique identifying and tracking numbers such as SKUs, and the like, prior to arrival of the organic material at the system 510. In certain embodiments, such input data may be transmitted remotely to the control system 536 before the organic material is received by the system 510. An external device or apparatus may determine the information and transmit the data to the control system 536 of the system 510.

Figure 6A:
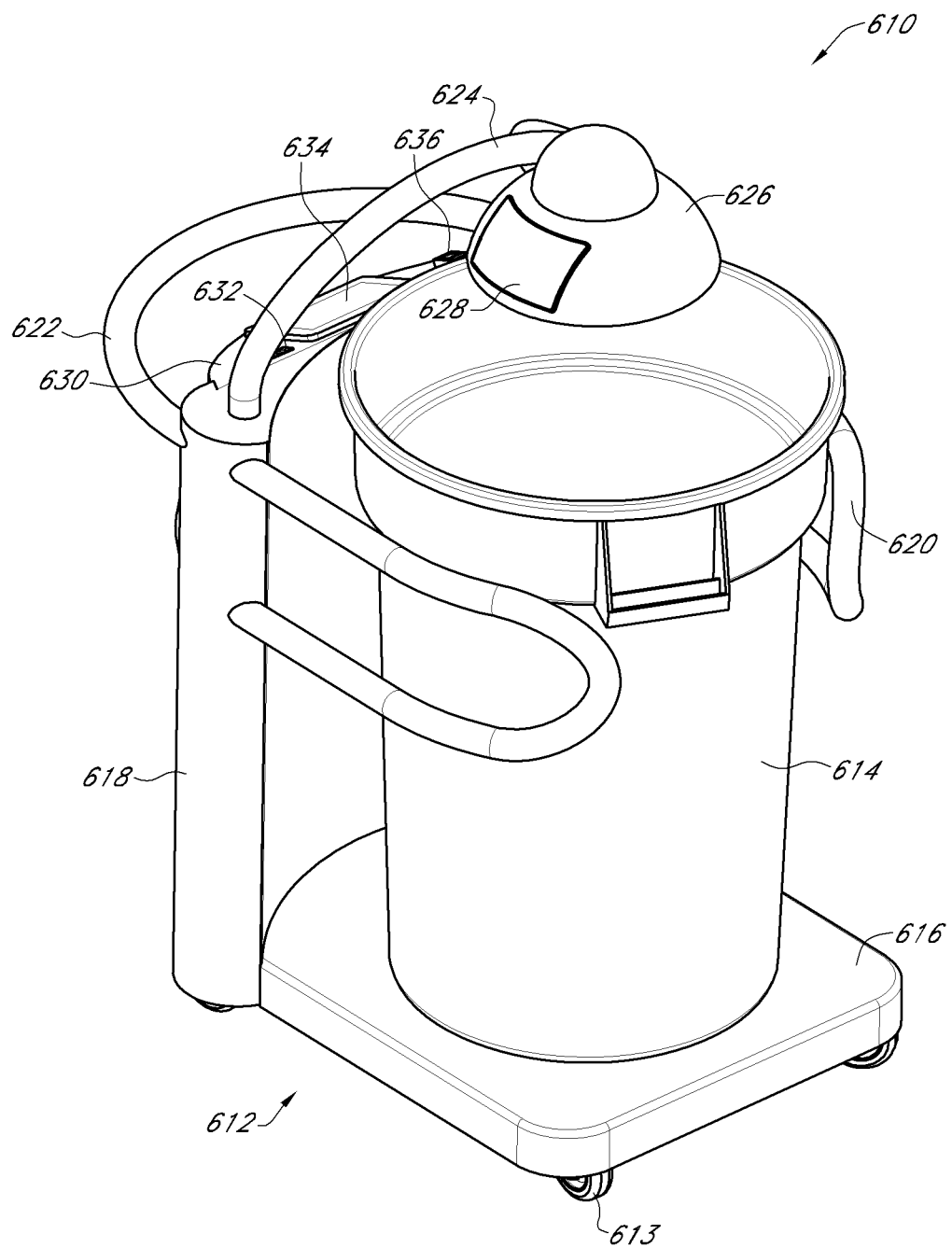
FIG. 6A is a perspective view illustrating one embodiment of a delivery apparatus for delivery of organic material, analysis of organic material, and transmission of data.
Figure 6B:
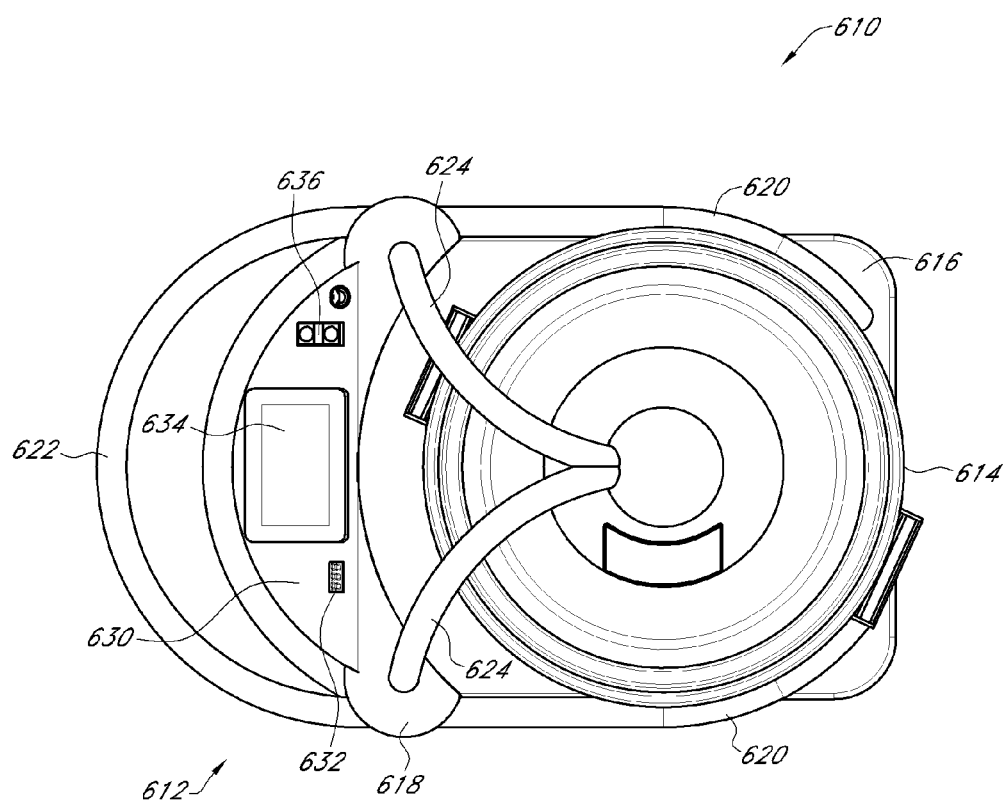
FIG. 6B is a top plan view illustrating one embodiment of a delivery apparatus for delivery of organic material, analysis of organic material, and transmission of data.
Figure 6C:
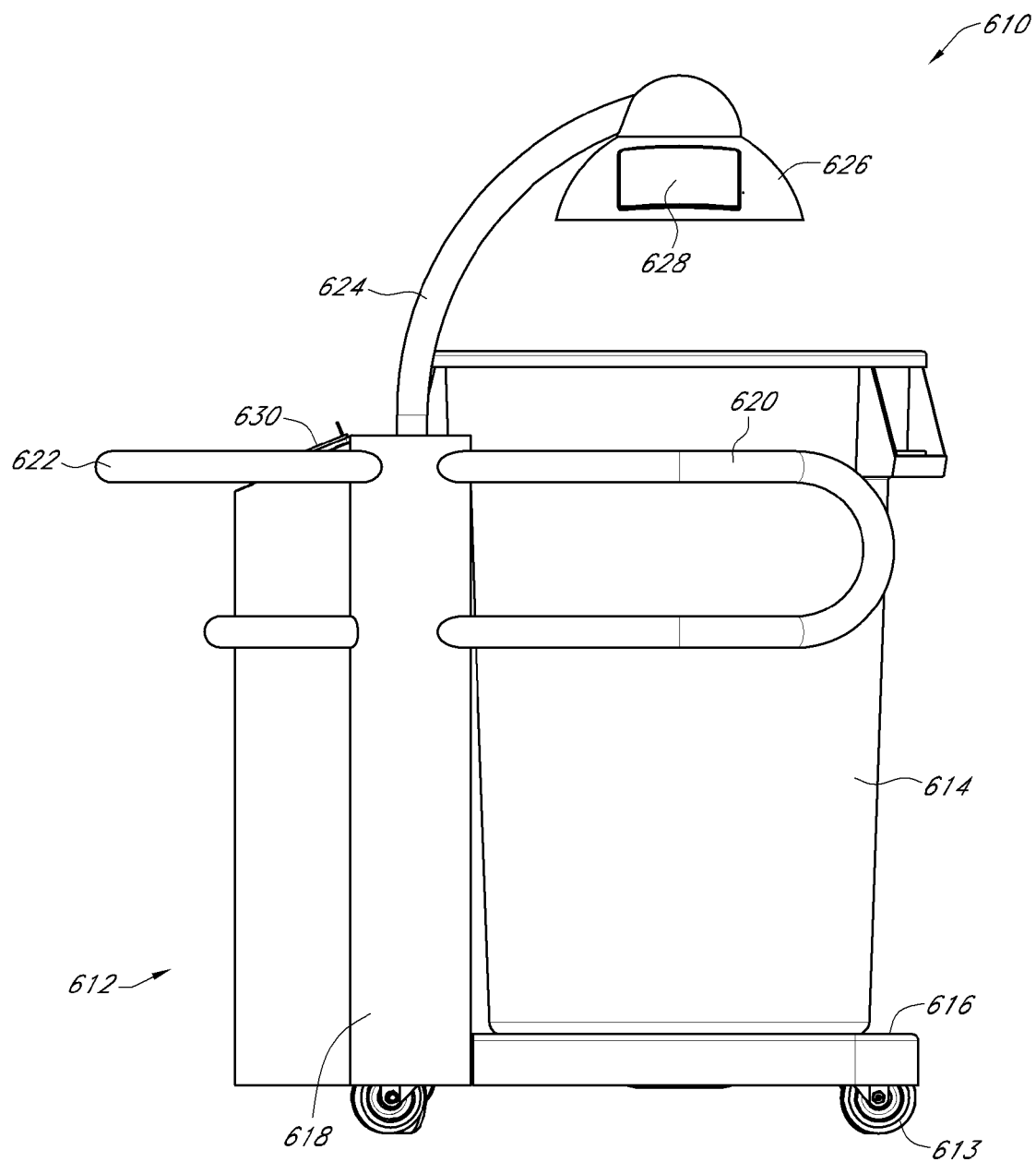
FIG. 6C is a side plan view illustrating one embodiment of a delivery apparatus for delivery of organic material, analysis of organic material, and transmission of data.

FIGS. 6A-6C illustrate embodiments of a delivery apparatus 610 for delivery of organic material, analysis of organic material, and transmission of data associated with the organic material. The apparatus shown in FIGS. 6A-6C contain multiple components for conducting the operations and methods described herein and it will be appreciated by one of skill in the art that the components are not limited to the arrangements shown in the figures, but can be arranged in alternative arrangements to accomplish the operations and methods disclosed.

A delivery apparatus 610 may be used to collect organic material from the premises and deliver it to the system 510 for processing, such as extracting the biochemical nutrients from the organic material, and then anabolizing and stabilizing the extracted biochemical nutrients. The delivery apparatus 610 may generate and collect data associated with the organic material, such as a category or type of organic material and the weight of the organic material. The delivery apparatus 610 may then deliver or transmit the collected data to the system 510, prior the delivery of the organic material to the system 510. For example, in one embodiment the delivery apparatus 610 may be used in a grocery store to collect food scraps. The delivery apparatus 610 may determine the category or type of food scraps added to the delivery apparatus 610, as well as the weight of the added to the delivery apparatus. The category and weight of the food scraps may be transmitted from the delivery apparatus 610 to the system 510, along with an identifier for the delivery apparatus 610 (or a bucket or container thereon). Thus, when the delivery apparatus 610 is taken to the system 510, the system 510 may receive as input the identifier from the delivery apparatus that was already sent to the system 510. Thus, the system 510 will be aware of the category and weight of the food scraps being deposited into the system 510 associated with this particular delivery apparatus 610. In this manner, the system 510 will already be set up with the correct data for comminution duration and water content needed for the food scraps when the food scraps are deposited into the system 510.

The delivery apparatus 610 illustrated in FIGS. 6A-6C may include a cart 612, having a platform 616. The platform 616 may be designed to carry a bucket or other container 614 positioned on the platform 616. The cart also may include a back panel 618. Securement arms 620 may extend from a portion of the back panel 618 to secure the bucket 614 on the platform 616. The platform 616 may be outfitted with a weighing device (such as, for example, a scale or load cells) to determine the weight of the bucket 614, along with any contents in the bucket 614. A tare weight of the empty bucket 614 may be established and recorded by the delivery apparatus 610 and the weighing device on the platform 616 may then determine the net weight of the contents put into the bucket 614.

The bucket 614 may be associated with a unique identifier such that any data generated and collected in relation to the contents of the bucket 614 may be associated with the unique identifier. In this manner, the unique identifier will allow the correct data to be associated with the organic material when the organic material is delivered to the system 510 for processing. The size of the bucket 614 may be a function of the premises in which the delivery apparatus is used and may more specifically be a function of the particular location in the premises. For example, in a grocery store, a 55 gallon bucket 614 may be appropriate for certain departments such as produce, deli, bakery, etc. Smaller or larger capacity buckets 614 may be used for various departments.

As shown in FIGS. 6A-6C, the back panel 618 of the cart 612 may include a control panel 630. The control panel 630 may include, for example, controls for operating various functions of the delivery apparatus 610 and may provide for display of data or information that is generated, transmitted, or received by the delivery apparatus 610. In certain embodiments, the delivery apparatus may contain a display screen 634 that may be touch-enabled to receive input from a user of the delivery apparatus 610. The control panel 630 may include a battery charge indicator 632 to indicate the status of the battery (not shown) that may provide power to the delivery apparatus 610. Also on the control panel 630, an on/off switch 636 may be used to turn the delivery apparatus on and off; the on/off switch 636 may be keyed to allow for a securement of the delivery apparatus 610 and prevent unintended uses within the confines of the premises.

The delivery apparatus 610 may also include a handle 622 by which the user of the apparatus 610 may direct the delivery apparatus 610. Under the platform 616, the cart 612 may include wheels 613, such as castor wheels, for maneuvering the delivery apparatus 610 through the premises.

Extending from the back panel 618 of the cart 612, one or more extension posts 624 may hold a sensor suite 626. The extension posts 624 may hold the sensor suite 626 over the bucket 614, such that the sensory apparatus in the sensor suite 626 may be in optical communication with the interior (and hence, the contents of) the bucket 614. The sensor suite 626 may be adjustable on the extension posts 624 to move up and down, rotate around, adjust laterally, or swivel.

The sensor suite 626 may include a touch screen display 628 to provide input to the sensor suite 626 and display information related to the sensor suite 626. The sensor suite 626 may include sensory apparatus to identify the contents of the organic material in the bucket 614, or otherwise obtain information related to the organic material placed in the bucket 614. The sensor suite may also identify the bucket 614 itself (by reading the unique identifier) and may identify information about the user of the delivery apparatus 610. The sensor suite 626 may include, for example, a barcode reader, an RFID reader, IR sensor, camera, and other optical sensors. The sensor suite 626 may receive, for example, the wavelength of electromagnetic radiation emitted from the organic material in the bucket 614. In another example, the sensory input device 626 may receive light data, color data, sound data, temperature data, smell data or other characteristic data of the organic material.

The data generated by the sensor suite 626 may be transmitted or delivered to the control system 536 of the system 510. The data may be transmitted to the system 510 wirelessly through any appropriate wireless communication protocol such as RF, Bluetooth, and/or 802.11a/b/g/n, etc. The control system 536 may determine an appropriate amount of liquid to combine with organic material based on data received from the delivery system 610. The control system 536 may also determine the appropriate comminution duration for the organic material based on data received from the delivery system 610.

In one example use, the delivery apparatus 610 may be used to collect food scraps from a particular department (deli, produce, etc.) of a grocery store. The delivery apparatus 610 may be positioned in the particular department. The user may cull the expired or otherwise unusable food from the department and place it in the bucket 614 of the delivery apparatus 610. Using the control panel 630 (or the touch-enabled display screen 634), the user may instruct the delivery apparatus 610 to weigh the food scraps placed in the bucket 614. Using the control panel 630 or the sensor suite touch screen 628, the user may instruct the delivery apparatus 610 to identify and categorize the food scraps in the bucket 614 of the delivery apparatus 610. This may be done using the sensor suite 626. The user may instruct the delivery apparatus to take a photo of the user and the food scraps in the bucket 614. The user may also instruct the delivery apparatus to wirelessly transmit the acquired data associated with the food scraps to the system 510, as well as an identifier for the delivery apparatus 610 or bucket 614. The user may eventually move the delivery apparatus 610 to the system 510 for processing of the food scraps. The user may input the identifier for the delivery apparatus 610 or bucket 614 into the system 510 and the system 510 will choose the appropriate comminution duration and water amount needed for optimal processing of the delivered food scraps, based on the data associated with the unique identifier already received by the system 510 from the delivery apparatus 610.

In certain embodiments, the system 510 may be equipped with a reader for reading the unique identifier associated with the delivered food scraps, thus the user would not be required to manually input the unique identifier of the bucket 614 or delivery apparatus 610 into the system 510.

In certain embodiments, the system 510 may be outfitted to automatically receive and dump the food scraps into the system 510 for processing. The system 510 may also be outfitted to automatically clean and sterilize the bucket 614 of the delivery apparatus 610 after it has automatically dumped the food scraps into the system 510.

The data collected by the delivery apparatus 610 may be tracked and aggregated by the premises. The premises has the ability with the delivery apparatus 610 to track and tabulate the quantity and type of food scraps being lost to waste. The collection of data allows the premises to adjust and optimize, for example, the premises conditions and purchasing decisions, to reduce the quantity of food lost to waste.

The data associated with the collected organic material which is collected by a given delivery apparatus 610 on a certain occasion may be used alone, or may be used with other aggregated data (from other locations in the premises, or other collection times, or other premises), to provide beneficial feedback information to the premises. As the delivery apparatus 610 may identify the category or type of organic material and the amount of organic material being discarded in the delivery apparatus 610, the user may use such data to optimize environmental and purchasing conditions to reduce the amount of organic material lost to waste. The data from the delivery apparatus 610 may be used to determine, for example, the loss of certain food categories at a grocery store. Over time, the changes in loss of a certain food category can be tracked and tabulated.

Such data from the delivery apparatus 610 may be used in conjunction with other data collected from the premises, such as the premises environmental data (e.g., the temperature settings in the given department of the grocery store), the day of the week the items are delivered and stocked, the quantity of product stocked in the department, or the wholesale quantity of the product purchased. The data may be transmitted to and stored at the system 510 or another central control system (e.g., computer system) for the premises.

In one non-limiting example, the delivery apparatus 610 may be used to collect and transmit data related to food waste in a given department, such as the produce department, of a grocery store. The contents and quantity of the food waste from the department may be stored and tabulated by the grocery store. The grocery store may then decide to adjust the environmental conditions of the particular department, or more specifically, the environmental conditions associated with the particular food item. For example, based on the data collected from the delivery system 610 regarding the quantity of certain fruits and vegetables lost to waste, the grocery store may decide to adjust the temperature at which certain fruits or vegetables are maintained. The grocery store may also decide to purchase less of a particular food item, such that less of the food item will be lost to food waste over time. The data from multiple grocery stores may also be aggregated and used to affect wholesale purchasing decisions for the grocery store chain.

Conditional language such as, among others, "can," "could," "might" or "may," unless specifically stated otherwise, are otherwise understood within the context as used in general to convey that certain embodiments include, while other embodiments do not include, certain features, elements and/or operations. Thus, such conditional language is not generally intended to imply that features, elements and/or operations are in any way required for one or more embodiments or that one or more embodiments necessarily include logic for deciding, with or without user input or prompting, whether these features, elements and/or operations are included or are to be performed in any particular embodiment.

Any process descriptions, elements or blocks in the flow diagrams described herein and/or depicted in the attached figures should be understood as potentially representing modules, segments, or portions of code which include one or more executable instructions for implementing specific logical functions or elements in the process. Alternate implementations are included within the scope of the embodiments described herein in which elements or functions may be deleted, executed out of order from that shown, or discussed, including substantially concurrently or in reverse order, depending on the functionality involved as would be understood by those skilled in the art.

It should be emphasized that many variations and modifications may be made to the above-described embodiments, the elements of which are to be understood as being among other acceptable examples. All such modifications and variations are intended to be included herein within the scope of this disclosure and protected by the following claims.

What is claimed is:

1. A system for stabilizing biochemical nutrients extracted from organic material, the system comprising:
   a comminution device configured to comminute the organic material into a slurry, the slurry containing liquid and particles of organic material, the biochemical nutrients from the organic material being extracted into the liquid;
   a liquid source fluidly coupled to the comminution device, configured to supply an amount of liquid to the comminution device;
   a biological tank configured to receive the slurry, wherein the biological tank contains a yeast in aerobic conditions, the yeast and the slurry forming a mixture and the yeast stabilizing the biochemical nutrients in the mixture; and
   an aeration system operably coupled to the biological tank to provide oxygen to the mixture and maintain an oxygen content in the mixture at approximately 0.5-3 ppm, the aeration system comprised of a blower coupled to a bubbler, the bubbler being comprised of a tube extending vertically through the mixture and having a distal end located in proximity to the bottom of the biological tank, the tube having an opening at the distal end through which the oxygen bubbles into the mixture, wherein the aeration system maintains the mixture in the biological tank in a non-turbulent quiescent state while providing oxygen to the mixture.

2. The system of claim 1, wherein the aeration system is configured to homogenously mix the mixture while the mixture is maintained in the non-turbulent quiescent state.

3. The system of claim 1, wherein the particles of organic material in the slurry have a particle size of less than approximately 3 mm.

4. The system of claim 1, further comprising a pump fluidly coupled to the comminution device and the biological tank, wherein the pump is configured to transport the slurry from the comminution device to the biological tank.

5. The system of claim 1, further comprising a processing tank fluidly coupled to the comminution device, configured to receive the slurry from the comminution device.

6. The system of claim 5, wherein the processing tank is configured to heat the slurry in order to pasteurize harmful microorganisms in the slurry.

7. The system of claim 5, wherein the processing tank is configured to receive hydrolytic enzymes to hydrolyze particles of organic material in the slurry.

8. The system of claim 1, wherein the yeast in the in the biological tank comprises *Saccharomyces cerevisiae*.

9. The system of claim 1, wherein the yeast is maintained in the mixture with a concentration of at least approximately 100,000 organisms per ml of mixture.

10. A method of stabilizing biochemical nutrients in organic material, comprising:
    receiving the organic material;
    extracting the biochemical nutrients from the organic material by comminuting the organic material in the presence of water;
    mixing the biochemical nutrients with yeast in a biological tank to form a mixture, the biological tank comprising a blower coupled to a bubbler, the bubbler being comprised of a tube extending vertically through the mixture and having a distal end located in proximity to the bottom of the biological tank, the tube having an opening at a distal end; and
    bubbling oxygen into the mixture in the biological tank by passing oxygen through the tube to exit the tube at the opening in the distal end and enter the mixture near the bottom of the biological tank, thereby maintaining the mixture in the biological tank in a non-turbulent quiescent state while providing oxygen to the mixture, and maintaining an oxygen content in the mixture at approximately 0.5-3 ppm.

11. The method of claim 10, wherein extracting the biochemical nutrients comprises forming a slurry of liquid and particles of organic material.

12. The method of claim 11, further comprising adding hydrolytic enzymes to the slurry to hydrolyze the particles of organic material.

13. The method of claim 11, further comprising heating the slurry to pasteurize harmful microorganisms in the slurry.

14. The method of claim 10, wherein the yeast is *Saccharomyces cerevisiae*.

15. The method of claim 10, further comprising monitoring the oxygen content of the mixture.

16. The method of claim 10, wherein comminuting the organic material comprises comminuting the organic material to a particle size of less than approximately 3 mm to extract the biochemical nutrients.

17. The method of claim 10, wherein mixing the biochemical nutrients with a yeast comprises anabolizing the biochemical nutrients to form a biomass, and wherein the percentage of biochemical nutrients that are stabilized as compared to biochemical nutrients that are anabolized is greater than approximately 85%.

18. The method of claim 10, wherein the mixture of yeast and biochemical nutrients is maintained in a stable state in aerobic conditions for at least 14 days.

19. The method of claim 10, further comprising maintaining the yeast in the mixture at a concentration of at least approximately 100,000 organisms per ml of mixture.

20. The method of claim 10, further comprising operating the biological tank at ambient temperature and ambient pressure.

* * * * *